United States Patent
Jung et al.

(10) Patent No.: US 9,476,070 B2
(45) Date of Patent: Oct. 25, 2016

(54) RECOMBINANT MICROORGANISM WITH ABILITY TO PRODUCE GLYCEROL, 3-HP, OR ACRYLIC ACID AND METHOD OF PRODUCING GLYCEROL, 3-HP, OR ACRYLIC ACID BY USING THE SAME

(71) Applicant: Samsung Electronics Co., Ltd., Suwon-si, Gyeonggi-do (KR)

(72) Inventors: Wonseok Jung, Seongnam-si (KR); Eunyoung Kim, Seoul (KR); Jinho Kang, Hwaseong-si (KR); Nagjong Kim, Daejeon (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/508,809

(22) Filed: Oct. 7, 2014

(65) Prior Publication Data
US 2015/0267226 A1 Sep. 24, 2015

(30) Foreign Application Priority Data
Mar. 24, 2014 (KR) ........................ 10-2014-0034131

(51) Int. Cl.
| | |
|---|---|
| *C12P 7/20* | (2006.01) |
| *C12N 9/00* | (2006.01) |
| *C12N 9/16* | (2006.01) |
| *C12N 9/88* | (2006.01) |
| *C12N 9/04* | (2006.01) |
| *C12N 9/02* | (2006.01) |

(52) U.S. Cl.
CPC .............. *C12P 7/20* (2013.01); *C12N 9/0006* (2013.01); *C12N 9/0008* (2013.01); *C12N 9/16* (2013.01); *C12N 9/88* (2013.01); *C12Y 301/02004* (2013.01); *C12Y 101/01006* (2013.01); *C12Y 102/01016* (2013.01); *C12Y 102/01024* (2013.01); *C12Y 301/03* (2013.01); *C12Y 402/01* (2013.01); *C12Y 402/0103* (2013.01); *Y02P 20/52* (2015.11)

(58) Field of Classification Search
None
See application file for complete search history.

(56) References Cited

U.S. PATENT DOCUMENTS

| | | |
|---|---|---|
| 6,358,716 B1 | 3/2002 | Bulthuis et al. |
| 7,005,291 B1 | 2/2006 | Nair et al. |
| 7,402,415 B2 | 7/2008 | Nair et al. |
| 2009/0053782 A1 | 2/2009 | Dundon et al. |

FOREIGN PATENT DOCUMENTS

EP  1 576 123 B1  12/2010

OTHER PUBLICATIONS

Zhang et al., "Tentative identiWcation of glycerol dehydrogenase as *Escherichia coli* K1 virulence factor cgID and its involvement in the pathogenesis of experimental neonatal meningitis", Med Microbiol Immunol (2009) 198:195-204. DOI 10.1007/s00430-009-0119-4.*
Eckford et al., "The reconstituted *Escherichia coli* MsbA protein displays lipid flippase activity", Biochem. J. (2010) 429, 195-203. doi:10.1042/BJ20100144.*
Niimi et al., "Metabolic engineering of 1,2-propanediol pathways in Corynebacterium glutamicum", Appl Microbiol Biotechnol (2011) 90:1721-1729. DOI 10.1007/s00253-011-3190-x.*
BRENDA Information for E.C. 1.1.1.6—Retrieved Jan. 28, 2016.*
BRENDA Information for E.C. 3.6.3.1—Retrieved Jan. 28, 2016.*
De Vries et al., "Glycerol dehydrogenase, encoded by gldB is essential for osmotolerance in *Aspergillus nidulans*", Molecular Microbiology 49(1): 131-141 (2003).
Jojima et al., "Identification of a HAD superfamily phosphatase, HdpA, involved in 1,3-dihydroxyacetone production during sugar catabolism in Corynebacterium glutamicum", *FEBS Letters*, 586: 4228-4232 (2012).
Liepins et al., "Enzymes for the NADPH-dependent reduction of dihydroxyacetone and D-glyceraldehyde and L-glyceraldehyde in the mould *Hypocrea jecorina*", FEBS Journal, 273: 4229-4235 (2006).
Subedi et al. "Role of GldA in dihydroxyacetone and methyloglyoxal metabolism of *Escherichia coli* K12," *FEMS Microbiol Lett*, 279, pp. 180-187 (2008).

* cited by examiner

Primary Examiner — Suzanne M Noakes
(74) Attorney, Agent, or Firm — Leydig, Voit & Mayer, Ltd.

(57) ABSTRACT

A recombinant microorganism having the ability to produce glycerol 3-HP, or acrylic acid, in which glycerol is produced from dihydroxyacetone phosphate (DHAP) via dihydroxyacetone (DHA) in a biosynthetic pathway, and a method of producing glycerol, 3-hydroxypropioninc acid (3-HP), or acrylic acid by using the recombinant microorganism.

18 Claims, 2 Drawing Sheets

SEQUENCE LISTING

```
<160> NUMBER OF SEQ ID NOS: 48

<210> SEQ ID NO 1
<211> LENGTH: 275
<212> TYPE: PRT
<213> ORGANISM: Corynebacterium glutamicum

<400> SEQUENCE: 1

Met Thr Val Asn Ile Ser Tyr Leu Thr Asp Met Asp Gly Val Leu Ile
1               5                   10                  15

Lys Glu Gly Glu Met Ile Pro Gly Ala Asp Arg Phe Leu Gln Ser Leu
            20                  25                  30

Thr Asp Asn Asn Val Glu Phe Met Val Leu Thr Asn Asn Ser Ile Phe
        35                  40                  45

Thr Pro Arg Asp Leu Ser Ala Arg Leu Lys Thr Ser Gly Leu Asp Ile
    50                  55                  60

Pro Pro Glu Arg Ile Trp Thr Ser Ala Thr Ala Thr Ala His Phe Leu
65                  70                  75                  80

Lys Ser Gln Val Lys Glu Gly Thr Ala Tyr Val Val Gly Glu Ser Gly
                85                  90                  95

Leu Thr Thr Ala Leu His Thr Ala Gly Trp Ile Leu Thr Asp Ala Asn
            100                 105                 110

Pro Glu Phe Val Val Leu Gly Glu Thr Arg Thr Tyr Ser Phe Glu Ala
        115                 120                 125

Ile Thr Thr Ala Ile Asn Leu Ile Leu Gly Gly Ala Arg Phe Ile Cys
    130                 135                 140

Thr Asn Pro Asp Val Thr Gly Pro Ser Pro Ser Gly Ile Leu Pro Ala
145                 150                 155                 160

Thr Gly Ser Val Ala Ala Leu Ile Thr Ala Ala Thr Gly Ala Glu Pro
                165                 170                 175

Tyr Tyr Ile Gly Lys Pro Asn Pro Val Met Met Arg Ser Ala Leu Asn
            180                 185                 190

Thr Ile Gly Ala His Ser Glu His Thr Val Met Ile Gly Asp Arg Met
        195                 200                 205

Asp Thr Asp Val Lys Ser Gly Leu Glu Ala Gly Leu Ser Thr Val Leu
    210                 215                 220

Val Arg Ser Gly Ile Ser Asp Asp Ala Glu Ile Arg Arg Tyr Pro Phe
225                 230                 235                 240

Arg Pro Thr His Val Ile Asn Ser Ile Ala Asp Leu Ala Asp Cys Trp
                245                 250                 255
```

Asp Asp Pro Phe Gly Asp Gly Ala Phe His Val Pro Asp Glu Gln Gln
            260                 265                 270

Phe Thr Asp
        275

<210> SEQ ID NO 2
<211> LENGTH: 828
<212> TYPE: DNA
<213> ORGANISM: Corynebacterium glutamicum
<220> FEATURE:
<221> NAME/KEY: gene
<222> LOCATION: (1)..(828)
<223> OTHER INFORMATION: hdpA gene

<400> SEQUENCE: 2
atgacagtga acatttcata tctgaccgac atggacggcg tcctcatcaa agagggcgag      60
atgattccgg gtgcagatcg tttcttcag tctctcaccg ataacaatgt ggagtttatg     120
gttttgacca acaactccat tttcaccccg agggatcttt ctgcacgtct taagacttcc    180
ggtttggata tcccgccgga gcgtatttgg acttctgcaa ccgccactgc tcacttcctg    240
aaatcccagg tcaaggaggg cacagcctat gttgttggcg agtctggtct gaccactgcg    300
ttgcataccg cggttggat tttgacggat gcaaatcctg agtttgttgt cctgggcgaa    360
acccgcacgt attccttcga ggcaatcacc actgctataa atctgatttt gggcggcgct    420
cgctttattt gcaccaaccc ggatgtaaca ggaccttcac caagtggcat tttgcctgct    480
actggctctg tcgcagcgct tattaccgca gctacaggcg ctgagcctta ttacatcggt    540
aagccaaacc ctgtgatgat gcgcagtgcg ctgaacacca tcggggcgca ttccgagcac    600
actgtcatga tcggcgaccg catggacacc gacgtgaaat ctggtttgga agccggcctg    660
agcaccgtgc tggttcgaag cggaatttcc gacgacgccg agatccgccg ctacccttc    720 cgcccaactc acgtgatcaa ttccatcgcc gatcttgccg attgctggga cgatccttc    780 ggtgacggtg catttcacgt accagatgag cagcagttca ctgactag                828

<210> SEQ ID NO 3
<211> LENGTH: 367
<212> TYPE: PRT
<213> ORGANISM: Escherichia coli
<220> FEATURE:
<221> NAME/KEY: MISC_FEATURE
<222> LOCATION: (1)..(367)
<223> OTHER INFORMATION: K gldA protein

<400> SEQUENCE: 3

Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
            20                  25                  30

Leu Val Val Gly Asp Lys Phe Val Leu Gly Phe Ala Gln Ser Thr Val
        35                  40                  45

Glu Lys Ser Phe Lys Asp Ala Gly Leu Val Val Glu Ile Ala Pro Phe
    50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Gly Lys Thr
                85                  90                  95

Leu Asp Thr Ala Lys Ala Leu Ala His Phe Met Gly Val Pro Val Ala
            100                 105                 110

Ile Ala Pro Thr Ile Ala Ser Thr Asp Ala Pro Cys Ser Ala Leu Ser
115                 120                 125

Val Ile Tyr Thr Asp Glu Gly Glu Phe Asp Arg Tyr Leu Leu Leu Pro
130                 135                 140

Asn Asn Pro Asn Met Val Ile Val Asp Thr Lys Ile Val Ala Gly Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Cys Thr Gln Ala Ala Leu Ala Leu Ala Glu Leu Cys Tyr Asn
        195                 200                 205

Thr Leu Leu Glu Glu Gly Glu Lys Ala Met Leu Ala Ala Glu Gln His
210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala Ala His Ala Val
                245                 250                 255

His Asn Gly Leu Thr Ala Ile Pro Asp Ala His His Tyr Tyr His Gly
            260                 265                 270

Glu Lys Val Ala Phe Gly Thr Leu Thr Gln Leu Val Leu Glu Asn Ala
        275                 280                 285

Pro Val Glu Glu Ile Glu Thr Val Ala Ala Leu Ser His Ala Val Gly
290                 295                 300

Leu Pro Ile Thr Leu Ala Gln Leu Asp Ile Lys Glu Asp Val Pro Ala
305                 310                 315                 320

Lys Met Arg Ile Val Ala Glu Ala Ala Cys Ala Glu Gly Glu Thr Ile
                325                 330                 335

His Asn Met Pro Gly Gly Ala Thr Pro Asp Gln Val Tyr Ala Ala Leu
            340                 345                 350

Leu Val Ala Asp Gln Tyr Gly Gln Arg Phe Leu Gln Glu Trp Glu
        355                 360                 365

<210> SEQ ID NO 4
<211> LENGTH: 1104
<212> TYPE: DNA
<213> ORGANISM: Escherichia coli
<220> FEATURE:
<221> NAME/KEY: gene
<222> LOCATION: (1)..(1104)
<223> OTHER INFORMATION: K gldA gene

<400> SEQUENCE: 4
atggaccgca ttattcaatc accgggtaaa tacatccagg cgctgatgtg gattaatcgt      60
ctgggcgaat acctgaagcc gctggcagaa cgctggttag tggtgggtga caaatttgtt     120
ttaggttttg ctcaatccac tgtcgagaaa gctttaaaag atgctggact ggtagtagaa     180
attgcgccgt ttggcggtga atgttcgcaa atgagatcg accgtctgcg tggcatcgcg      240
gagactgcgc agtgtggcgc aattctcggt atcggtggcg aaaaaccct cgatactgcc      300 aaagcactgg cacatttcat gggtgttccg gtagcgatcg caccgactat cgcctctacc     360
gatgcaccgt gcagcgcatt gtctgttatc tacaccgatg agggtgagtt tgaccgctat     420
ctgctgttgc caaataaccc gaatatggtc attgtcgaca ccaaaatcgt cgctggcgca     480
cctgcacgtc tgttagcggc gggtatcggc gatgcgctgg caacctggtt tgaagcgcgt     540
gcctgctctc gtagcggcgc gaccaccatg gcgggcggca agtgcaccca ggctgcgctg     600

```
gcactggctg aactgtgcta caacaccctg ctggaagaag gcgaaaaagc gatgcttgct      660
gccgaacagc atgtagtgac tccggcgctg gagcgcgtga ttgaagcgaa cacctatttg      720
agcggtgttg gttttgaaag tggtggtctg gctgcggcgc acgcagtgca taacggcctg      780
accgctatcc cggacgcgca tcactattat cacggtgaaa aagtggcatt cggtacgctg      840
acgcagctgg ttctggaaaa tgcgccggtg gaggaaatcg aaaccgtagc tgcccttagc      900
catgcggtag gtttgccaat aactctcgct caactggata ttaaagaaga tgtcccggcg      960
aaaatgcgaa ttgtggcaga agcggcatgt gcagaaggtg aaaccattca caacatgcct     1020
ggcggcgcga cgccagatca ggtttacgcc gctctgctgg tagccgacca gtacggtcag     1080
cgtttcctgc aagagtggga ataa                                            1104
```

<210> SEQ ID NO 5
<211> LENGTH: 1665
<212> TYPE: DNA
<213> ORGANISM: Ilyobacter polytropus
<220> FEATURE:
<221> NAME/KEY: gene
<222> LOCATION: (1)..(1665)
<223> OTHER INFORMATION: dhaB1 gene

<400> SEQUENCE: 5

```
atgaaatcaa aaagatttga agtattgaag gaacgtcctg taaataaaga tggctttata       60
agtgaatgga tagaagaagg actaatcgca atggaaagtc ctaacgatcc taatccaagt      120
ttgaaaatag aaaatggtca aataacagag ttagacggta aaagcagaga gaatttgac       180 atgatcgaca gatttatagc agattatgca ataaatatgg aaaatgctga aaaagctatg      240
aaaatgtcat ctatggaaat atctaaaaaa ctagtagaca taaatgtatc aagagatgaa      300
gtgctggaaa taacaacagg aattacccca gcaaaaataa ttaaagttat ggaacacatg      360
aatgttgtag agatgatgat ggccgtacaa aaaatgagag ccagaaaaac tccttccaat      420
cagtgtcatg taactaactt gagagacaat cctgtattaa ttgccgctga tgctgccgaa      480
gcgtcagtaa gaggttttga tgaacaggag actacaatcg gtatagtaag atatgcacct      540
ttcaatgcca tctcaatatt tgtaggttca caagtaggta gaggaggaat actgactcag      600
tgttctgtag aagaagctac tgaattagag cttggaatga aggattcac aagttatgca      660 gaaacagtgt ctgtatatgg tacagagcaa gtgtttatag acggtgacga cactccttgg      720
tcaaaagcct tccttgcttc agcatatgca tcaagaggat taaaaatgag atttacatct      780
ggaactggtt cagaggctct tatgggaaat gctgaaggga atcaatgct ttaccttgaa      840 gcaagatgta tctacgtaac aagagggtct ggagtacaag gactacaaaa tggttctgta      900
agctgcatag ggatgcctgg gtcactacct ggaggaataa gggctgtact ggctgaaaac      960
ctgatagcaa tgttacttga cttagaatgt gcatcagcaa atgaccagac attctctcac     1020
tcagaatata gaaggacagc aagaactcta atgcagatgc ttcctggaac agacttcata     1080
ttctcaggat atagtgccgt accaaactgt gataacatgt ttgctggatc aaattttgat     1140
gcagaggatt ttgatgacta taatgctctt cagagagacc ttaaaataga cggtggttta     1200
aaacctgtaa ctgaagatga gattgtcaaa gtaagaaata agcagccag agcaatacag     1260 gggttattca agaacttga tcttcctgaa ataacagatg aagaagtgga agcagcaaca     1320
tatgcccacg gaagtgttga tatgcctgca agaaatgtgg ttgaagattt aaaagcggca     1380
gaagaacttt taagctctgg aataacagga gtagatcttg ttaaaggact tagcagaagc     1440
```

```
ggatttgacg atgtagctga gcatgtttta ggtatgttaa acagagagt ttcaggagat    1500 tacctgcaaa cttcagctat attagacaaa ggctttaaaa taaagagtgc cataaacgat   1560
agaaatgatt acatgggtcc tggaagcgga tatagaataa gcgaggaaag atgggaagag   1620
atcaaaaata tcccatcagc tataaaacca gaaagtatag aatag                  1665
```

<210> SEQ ID NO 6
<211> LENGTH: 564
<212> TYPE: DNA
<213> ORGANISM: Ilyobacter polytropus
<220> FEATURE:
<221> NAME/KEY: gene
<222> LOCATION: (1)..(564)
<223> OTHER INFORMATION: dhaB2 gene

<400> SEQUENCE: 6

```
atggaaaata aatttgtacc atctgtaaag atagaagaaa tcggagaagc aaaaaaagga    60
agcagatctg aagaagtagt tataggactg gctcctgcat ttaaaaaatt tcaacataaa   120
acaataacag atgtccctca cgatgaagtc ctgactgaac ttatcgcagg tatagaggaa   180
gagggattaa aggcaagaat cgtaagagta acaagaactt ctgatgtttc atttatggcg   240
ctggatgctg caaagttaag tggttctgga ataggaatag gaattcagtc aaagggaaca   300
acagtaatcc accaaaagga tctgcttcct ctaaacaatc tagaacttt ccacaggct    360 ccactattaa cacctgaaac attcagatta ataggaaaaa atgctgcaaa atatgcaaag   420
ggagaatctc caaatccagt acctgtagcc agtgaccaga tggcgagacc taaatatcag   480
gcaaaagcag cattactaca tataaaagag acaaaacatg tcgttcaaca cggaaaacca   540
gtagagataa agtatgaatt ttag                                          564
```

<210> SEQ ID NO 7
<211> LENGTH: 432
<212> TYPE: DNA
<213> ORGANISM: Ilyobacter polytropus
<220> FEATURE:
<221> NAME/KEY: gene
<222> LOCATION: (1)..(432)
<223> OTHER INFORMATION: dhaB3 gene

<400> SEQUENCE: 7

```
atgaatatag atgttaaaaa tataaatcca atctctgatt atccattagg agaaaagaga    60
aaagaatggt tgaaaacatc cacaggtaaa actttggatg aaataacttt agaaaatgta   120
ataaatggag atataaagcc tgaagatata agaatctcac ctgaaactct aaaattacag   180
ggagagatag caaagaaagg taacaggcca actataacaa gaactttga aagagccagt    240 gaaatggttg ccattccaga tgataaaata ttagcaactt acaacgcttt gagaccttac   300
agatcttcaa aggaagaatt atttgaaata gccgatgaac tagaaagtaa gtattcagct   360
gttgtaatat ctgcatttat caaggaagcc gcagaagttt atgaacaaag aggtcaactt   420
agaaaagatt ag                                                       432
```

<210> SEQ ID NO 8
<211> LENGTH: 490
<212> TYPE: PRT
<213> ORGANISM: Escherichia coli
<220> FEATURE:
<221> NAME/KEY: MISC_FEATURE
<222> LOCATION: (1)..(490)
<223> OTHER INFORMATION: gabD1

<400> SEQUENCE: 8

-continued

```
Met Thr Ile Asn Val Ser Glu Leu Leu Ala Lys Val Pro Thr Gly Leu
1               5                   10                  15

Leu Ile Gly Asp Ser Trp Val Glu Ala Ser Asp Gly Gly Thr Phe Asp
                20                  25                  30

Val Glu Asn Pro Ala Thr Gly Glu Thr Ile Ala Thr Leu Ala Ser Ala
                35                  40                  45

Thr Ser Glu Asp Ala Leu Ala Ala Leu Asp Ala Ala Cys Ala Val Gln
    50                  55                  60

Ala Glu Trp Ala Arg Met Pro Ala Arg Glu Arg Ser Asn Ile Leu Arg
65                  70                  75                  80

Arg Gly Phe Glu Leu Val Ala Glu Arg Ala Glu Phe Ala Thr Leu
                85                  90                  95

Met Thr Leu Glu Met Gly Lys Pro Leu Ala Glu Ala Arg Gly Glu Val
                100                 105                 110

Thr Tyr Gly Asn Glu Phe Leu Arg Trp Phe Ser Glu Glu Ala Val Arg
    115                 120                 125

Leu Tyr Gly Arg Tyr Gly Thr Thr Pro Glu Gly Asn Leu Arg Met Leu
    130                 135                 140

Thr Ala Leu Lys Pro Val Gly Pro Cys Leu Leu Ile Thr Pro Trp Asn
145                 150                 155                 160

Phe Pro Leu Ala Met Ala Thr Arg Lys Val Ala Pro Ala Ile Ala Ala
                165                 170                 175

Gly Cys Val Met Val Leu Lys Pro Ala Arg Leu Thr Pro Leu Thr Ser
                180                 185                 190

Gln Tyr Phe Ala Gln Thr Met Leu Asp Ala Gly Leu Pro Ala Gly Val
    195                 200                 205

Leu Asn Val Val Ser Gly Ala Ser Ala Ser Ala Ile Ser Asn Pro Ile
    210                 215                 220

Met Glu Asp Asp Arg Leu Arg Lys Val Ser Phe Thr Gly Ser Thr Pro
225                 230                 235                 240

Val Gly Gln Gln Leu Leu Lys Lys Ala Asp Lys Val Leu Arg Thr
                245                 250                 255

Ser Met Glu Leu Gly Gly Asn Ala Pro Phe Ile Val Phe Glu Asp Ala
    260                 265                 270

Asp Leu Asp Leu Ala Ile Glu Gly Ala Met Gly Ala Lys Met Arg Asn
    275                 280                 285

Ile Gly Glu Ala Cys Thr Ala Ala Asn Arg Phe Leu Val His Glu Ser
    290                 295                 300

Val Ala Asp Glu Phe Gly Arg Arg Phe Ala Ala Arg Leu Glu Glu Gln
305                 310                 315                 320

Val Leu Gly Asn Gly Leu Asp Glu Gly Val Thr Val Gly Pro Leu Val
                325                 330                 335

Glu Glu Lys Ala Arg Asp Ser Val Ala Ser Leu Val Asp Ala Ala Val
    340                 345                 350

Ala Glu Gly Ala Thr Val Leu Thr Gly Gly Lys Ala Gly Thr Gly Ala
                355                 360                 365

Gly Tyr Phe Tyr Glu Pro Thr Val Leu Thr Gly Val Ser Thr Asp Ala
    370                 375                 380

Ala Ile Leu Asn Glu Glu Ile Phe Gly Pro Val Ala Pro Ile Val Thr
385                 390                 395                 400

Phe Gln Thr Glu Glu Glu Ala Leu Arg Leu Ala Asn Ser Thr Glu Tyr
                405                 410                 415
```

```
Gly Leu Ala Ser Tyr Val Phe Thr Gln Asp Thr Ser Arg Ile Phe Arg
                420                 425                 430

Val Ser Asp Gly Leu Glu Phe Gly Leu Val Gly Val Asn Ser Gly Val
            435                 440                 445

Ile Ser Asn Ala Ala Ala Pro Phe Gly Gly Val Lys Gln Ser Gly Met
    450                 455                 460

Gly Arg Glu Gly Gly Leu Glu Gly Ile Glu Glu Tyr Thr Ser Val Gln
465                 470                 475                 480

Tyr Ile Gly Ile Arg Asp Pro Tyr Ala Gly
                485                 490

<210> SEQ ID NO 9
<211> LENGTH: 453
<212> TYPE: PRT
<213> ORGANISM: Escherichia coli
<220> FEATURE:
<221> NAME/KEY: MISC_FEATURE
<222> LOCATION: (1)..(453)
<223> OTHER INFORMATION: gabD2

<400> SEQUENCE: 9

Met Ser Leu Thr Phe Pro Val Ile Asn Pro Ser Asp Gly Ser Thr Ile
1               5                   10                  15

Thr Glu Leu Glu Asn His Asp Ser Thr Gln Trp Met Ser Ala Leu Ser
                20                  25                  30

Asp Ala Val Ala Ala Gly Pro Ser Trp Ala Ala Lys Thr Pro Arg Glu
            35                  40                  45

Arg Ser Val Val Leu Thr Ala Ile Phe Glu Ala Leu Thr Glu Arg Ala
    50                  55                  60

Gln Glu Leu Ala Glu Ile Ile His Leu Glu Ala Gly Lys Ser Val Ala
65                  70                  75                  80

Glu Ala Leu Gly Glu Val Ala Tyr Gly Ala Glu Tyr Phe Arg Trp Phe
                85                  90                  95

Ala Glu Glu Ala Val Arg Leu Pro Gly Arg Tyr Gly Gln Ser Pro Ser
            100                 105                 110

Gly Ile Gly His Ile Ala Val Thr Arg Ala Pro Val Gly Pro Val Leu
    115                 120                 125

Ala Ile Thr Pro Trp Asn Phe Pro Ile Ala Met Ala Thr Arg Lys Ile
130                 135                 140

Ala Pro Ala Leu Ala Ala Gly Cys Pro Val Leu Val Lys Pro Ala Ser
145                 150                 155                 160

Glu Thr Pro Leu Thr Met Val Lys Val Gly Glu Ile Ile Ala Ser Val
                165                 170                 175

Phe Asp Thr Phe Asn Ile Pro Gln Gly Leu Val Ser Ile Thr Thr
            180                 185                 190

Thr Arg Asp Ala Glu Leu Ser Ala Glu Leu Met Ala Asp Pro Arg Leu
    195                 200                 205

Ala Lys Val Thr Phe Thr Gly Ser Thr Asn Val Gly Arg Ile Leu Val
210                 215                 220

Arg Gln Ser Ala Asp Arg Leu Leu Arg Thr Ser Met Glu Leu Gly Gly
225                 230                 235                 240

Asn Ala Ala Phe Val Ile Asp Glu Ala Ala Asp Leu Asp Glu Ala Val
                245                 250                 255

Ser Gly Ala Ile Ala Ala Lys Leu Arg Asn Ala Gly Gln Val Cys Ile
            260                 265                 270

Ala Ala Asn Arg Phe Leu Val His Glu Ser Arg Ala Ala Glu Phe Thr
```

```
              275                 280                 285
Ser Lys Leu Ala Thr Ala Met Gln Asn Thr Pro Ile Gly Pro Val Ile
290                 295                 300

Ser Ala Arg Gln Arg Asp Arg Ile Ala Ala Leu Val Asp Glu Ala Ile
305                 310                 315                 320

Thr Asp Gly Ala Arg Leu Ile Ile Gly Gly Glu Val Pro Asp Gly Ser
                325                 330                 335

Gly Phe Phe Tyr Pro Ala Thr Ile Leu Ala Asp Val Pro Ala Gln Ser
                340                 345                 350

Arg Ile Val His Glu Glu Ile Phe Gly Pro Val Ala Thr Ile Ala Thr
                355                 360                 365

Phe Thr Asp Leu Ala Glu Gly Val Ala Gln Ala Asn Ser Thr Glu Phe
370                 375                 380

Gly Leu Ala Ala Tyr Gly Phe Ser Asn Asn Val Lys Ala Thr Gln Tyr
385                 390                 395                 400

Met Ala Glu His Leu Glu Ala Gly Met Val Gly Ile Asn Arg Gly Ala
                405                 410                 415

Ile Ser Asp Pro Ala Ala Pro Phe Gly Gly Ile Gly Gln Ser Gly Phe
                420                 425                 430

Gly Arg Glu Gly Gly Thr Glu Gly Ile Glu Glu Tyr Leu Ser Val Arg
                435                 440                 445

Tyr Leu Ala Leu Pro
    450
```

<210> SEQ ID NO 10
<211> LENGTH: 521
<212> TYPE: PRT
<213> ORGANISM: Escherichia coli
<220> FEATURE:
<221> NAME/KEY: MISC_FEATURE
<222> LOCATION: (1)..(521)
<223> OTHER INFORMATION: gabD3

<400> SEQUENCE: 10

```
Met Ile Lys Arg Leu Pro Leu Gly Pro Leu Pro Lys Glu Leu His Gln
1               5                   10                  15

Thr Leu Leu Asp Leu Thr Ala Asn Ala Gln Asp Ala Ala Lys Val Glu
                20                  25                  30

Val Ile Ala Pro Phe Thr Gly Glu Thr Leu Gly Phe Val Phe Asp Gly
            35                  40                  45

Asp Glu Gln Asp Val Glu His Ala Phe Ala Leu Ser Arg Ala Ala Gln
50                  55                  60

Lys Lys Trp Val His Thr Thr Ala Val Glu Arg Lys Lys Ile Phe Leu
65                  70                  75                  80

Lys Phe His Asp Leu Val Leu Lys Asn Arg Glu Leu Leu Met Asp Ile
                85                  90                  95

Val Gln Leu Glu Thr Gly Lys Asn Arg Ala Ser Ala Ala Asp Glu Val
            100                 105                 110

Leu Asp Val Ala Ile Thr Thr Arg Phe Tyr Ala Asn Asn Ala Gly Lys
        115                 120                 125

Phe Leu Asn Asp Lys Lys Arg Pro Gly Ala Leu Pro Ile Ile Thr Lys
130                 135                 140

Asn Thr Gln Gln Tyr Val Pro Lys Gly Val Val Gly Gln Ile Thr Pro
145                 150                 155                 160

Trp Asn Tyr Pro Leu Thr Leu Gly Val Ser Asp Ala Val Pro Ala Leu
                165                 170                 175
```

Leu Ala Gly Asn Ala Val Ala Lys Pro Asp Leu Ala Thr Pro Phe
                180                 185                 190

Ser Cys Leu Ile Met Val His Leu Ile Glu Ala Gly Leu Pro Arg
            195                 200                 205

Asp Leu Met Gln Val Val Thr Gly Pro Gly Asp Ile Val Gly Gly Ala
    210                 215                 220

Ile Ala Ala Gln Cys Asp Phe Leu Met Phe Thr Gly Ser Thr Ala Thr
225                 230                 235                 240

Gly Arg Ile Leu Gly Arg Thr Met Gly Glu Arg Leu Val Gly Phe Ser
                245                 250                 255

Ala Glu Leu Gly Gly Lys Asn Pro Leu Ile Val Ala Lys Asp Ala Asp
                260                 265                 270

Leu Asp Lys Val Glu Ala Glu Leu Pro Gln Ala Cys Phe Ser Asn Ser
            275                 280                 285

Gly Gln Leu Cys Val Ser Thr Glu Arg Ile Tyr Val Glu Glu Asp Val
    290                 295                 300

Tyr Glu Glu Val Ile Ala Arg Phe Ser Lys Ala Ala Lys Ala Met Ser
305                 310                 315                 320

Ile Gly Ala Gly Phe Glu Trp Lys Tyr Glu Met Gly Ser Leu Ile Asn
                325                 330                 335

Gln Ala Gln Leu Asp Arg Val Ser Thr Phe Val Asp Gln Ala Lys Ala
                340                 345                 350

Ala Gly Ala Thr Val Leu Cys Gly Gly Lys Ser Arg Pro Asp Ile Gly
            355                 360                 365

Pro Phe Phe Tyr Glu Pro Thr Val Leu Ala Asp Val Pro Glu Gly Thr
    370                 375                 380

Pro Leu Leu Thr Glu Glu Val Phe Gly Pro Val Val Phe Ile Glu Lys
385                 390                 395                 400

Val Ala Thr Leu Glu Glu Ala Val Asp Lys Ala Asn Gly Thr Pro Tyr
                405                 410                 415

Gly Leu Asn Ala Ser Val Phe Gly Ser Ser Glu Thr Gly Asn Leu Val
                420                 425                 430

Ala Gly Gln Leu Glu Ala Gly Gly Ile Gly Ile Asn Asp Gly Tyr Ala
            435                 440                 445

Ala Thr Trp Ala Ser Val Ser Thr Pro Leu Gly Gly Met Lys Gln Ser
    450                 455                 460

Gly Leu Gly His Arg His Gly Ala Glu Gly Ile Thr Lys Tyr Ala Glu
465                 470                 475                 480

Ile Arg Asn Ile Ala Glu Gln Arg Trp Met Ser Met Arg Gly Pro Ala
                485                 490                 495

Lys Met Pro Arg Lys Val Tyr Ser Asp Thr Val Ala Thr Ala Leu Lys
                500                 505                 510

Leu Gly Lys Ile Phe Lys Val Leu Pro
        515                 520

<210> SEQ ID NO 11
<211> LENGTH: 1473
<212> TYPE: DNA
<213> ORGANISM: Escherichia coli
<220> FEATURE:
<221> NAME/KEY: misc_feature
<222> LOCATION: (1)..(1473)
<223> OTHER INFORMATION: gabD1

<400> SEQUENCE: 11

| | |
|---|---|
| atgactatta atgtctccga actacttgcc aaagtcccca cgggtctact gattggtgat | 60 |
| tcctgggtgg aagcatccga cggcggtact ttcgatgtgg aaaacccagc gacgggtgaa | 120 |
| acaatcgcaa cgctcgcgtc tgctacttcc gaggatgcac tggctgctct tgatgctgca | 180 |
| tgcgctgttc aggccgagtg ggctaggatg ccagcgcgcg agcgttctaa tattttacgc | 240 |
| cgcggttttg agctcgtagc agaacgtgca gaagagttcg ccaccctcat gaccttggaa | 300 |
| atgggcaagc ctttggctga agctcgcggc gaagtcacct acggcaacga attcctgcgc | 360 |
| tggttctctg aggaagcagt tcgtctgtat ggccgttacg gaaccacacc agaaggcaac | 420 |
| ttgcggatgc tgaccgccct caagccagtt ggccgtgcc tcctgatcac cccatggaac | 480 |
| ttcccactag caatggctac ccgcaaggtc gcacctgcga tcgctgcagg ttgtgtcatg | 540 |
| gtgctcaagc cagctcgact taccccgctg acctcccagt attttgctca gaccatgctt | 600 |
| gatgccggtc ttccagcagg tgtcctcaat gtggtctccg gtgcttccgc tctgcgatt | 660 |
| tccaacccga ttatggaaga cgatcgcctt cgtaaagtct ccttcaccgg ctccacccca | 720 |
| gttggccagc agctgctcaa aaaggctgcc gataaagttc tgcgcacctc catggaactt | 780 |
| ggtggcaacg caccttttcat tgtcttcgag gacgccgacc tagatctcgc gatcgaaggt | 840 |
| gccatgggtg ccaaaatgcg caacatcggc gaagcttgca ccgcagccaa ccgtttctta | 900 |
| gtccacgaat ccgtcgccga tgaattcggc cgtcgcttcg ctgcccgcct gaagagcaa | 960 |
| gtcctaggca acgcctcga cgaaggcgtc accgtgggcc cctggttga ggaaaaagca | 1020 |
| cgagacagcg ttgcatcgct tgtcgacgcc gccgtcgccg aaggtgccac cgtcctcacc | 1080 |
| ggcggcaagg ccggcacagg tgcaggctac ttctacgaac caacggtgct cacgggagtt | 1140 |
| tcaacagatg cggctatcct gaacgaagag atcttcggtc ccgtcgcacc gatcgtcacc | 1200 |
| ttccaaaccg aggaagaagc cctgcgtcta gccaactcca ccgaatacgg actggcctcc | 1260 |
| tatgtgttca cccaggacac ctcacgtatt ttccgcgtct ccgatggtct cgagttcggc | 1320 |
| ctagtgggcg tcaattccgg tgtcatctct aacgctgctg cacctttgg tggcgtaaaa | 1380 |
| caatccggaa tgggccgcga aggtggtctc gaaggaatcg aggagtacac ctccgtgcag | 1440 |
| tacatcggta tccgggatcc ttacgccggc tag | 1473 |

<210> SEQ ID NO 12
<211> LENGTH: 1362
<212> TYPE: DNA
<213> ORGANISM: Escherichia coli
<220> FEATURE:
<221> NAME/KEY: gene
<222> LOCATION: (1)..(1362)
<223> OTHER INFORMATION: gabD2 gene

<400> SEQUENCE: 12

| | |
|---|---|
| gtgtctttga ccttcccagt aatcaacccc agcgatggct ccaccatcac cgagctagaa | 60 |
| aaccacgatt ccacccagtg gatgtccgcg ctctctgatg cagttgcagc tggtccttca | 120 |
| tgggctgcga aaactccccg cgaaagatcc gtggtactca ccgcaatctt cgaagcactg | 180 |
| accgaacgcg cccaagaact tgcagagatc atccacctgg aagctggaaa atccgttgca | 240 |
| gaagctcttg gtgaagtcgc ttatggtgca gaatacttcc gttggtttgc ggaagaagca | 300 |
| gtgcgcctgc ccggccgcta cggacagtca ccttccggaa tcggtcacat cgccgtcacc | 360 |
| cgcgcacccg tgggaccagt gctggcgatc accccatgga atttccccat cgccatggcc | 420 |
| acccgcaaaa tcgccccagc cctggccgct ggttgccccg tgttggtgaa acctgcttcc | 480 |
| gaaacccccac tgaccatggt caaagtgggg gagatcatcg cctccgtctt tgataccttt | 540 |

```
aatatcccgc agggcttggt ctcaatcatc accaccactc gagatgcaga gctatcggca      600
gaactcatgg ctgatcctcg cttggctaaa gtcaccttca ctggatcaac caacgtggga      660
cgcatcctgg tccgccaatc cgcggaccga ctgctgcgca cctccatgga actcggcgga      720
aatgcagctt ttgttatcga cgaagccgca gacctcgacg aagccgtatc cggtgccatc      780
gccgcaaaac tccgcaacgc cggccaagta tgcatcgcag ctaaccgttt cttggttcat      840
gaatcccgcg ctgccgaatt cacctcaaag ctggcgacac ccatgcagaa cactcccatt      900
gggccggtga tttctgcccg ccaacgcgac cggatcgcag cactagtgga tgaagccatc      960
accgacggcg cccgcctcat catcggtggg gaggtccccg acggctccgg cttcttctat     1020
ccagccacca tcttggccga tgtccctgca cagtcacgga ttgtgcatga ggaaatcttc     1080
ggacctgtgg ccaccattgc cactttcacc gacttggccg aaggcgttgc acaagcaaat     1140
tccaccgaat tcggcctcgc agcctacgga ttcagcaaca atgtgaaagc aacacagtac     1200
atggcggaac acttggaagc cggaatggtc ggaatcaaca gaggcgccat ctctgaccca     1260
gcagcacctt ttggcggcat cggacaatcc ggcttcggca gagaaggcgg aaccgaagga     1320
atcgaagaat atctctccgt gcgttacctc gctttgccgt ga                        1362
```

<210> SEQ ID NO 13
<211> LENGTH: 1566
<212> TYPE: DNA
<213> ORGANISM: Escherichia coli
<220> FEATURE:
<221> NAME/KEY: gene
<222> LOCATION: (1)..(1566)
<223> OTHER INFORMATION: gabD3 gene

<400> SEQUENCE: 13

```
atgatcaaac gtcttccttt aggtccgctg cctaaagaac ttcatcagac tctgcttgat       60
ctgaccgcaa atgcccaaga tgcggcgaaa gtggaggtta tagcgccatt tactggcgag      120
accctcggat ttgttttttga tggtgatgag caagacgtcg agcatgcttt tgcactttca      180
agggcagccc agaaaaagtg ggtgcacacc acggcagtgg aacggaagaa gatcttcctg      240
aagtttcatg atctggtatt gaaaaaccgt gagctgctca tggacatcgt gcagttggaa      300
acaggcaaaa atcgagcatc ggctgccgat gaggtgttgg acgttgcgat caccacccgc      360
ttctacgcaa acaatgcagg aaagttttta aatgacaaga acgccccggg cgcgcttccg      420
atcatcacga aaaacacaca acagtatgtg cccaagggag tggtcgggca gatcacgccg      480
tggaattacc ctttaacttt gggagtatct gatgctgttc cggcgctgct ggcaggaaac      540
gcagtggtgg ctaaacctga cctcgcgaca cctttctcct gcttgatcat ggtgcacctg      600
ctcattgaag ccggtctgcc gcgtgatttg atgcaggttg tcaccggccc tggcgatatt      660
gttggcggtg cgattgcagc tcagtgtgat ttcctcatgt tcactggatc cacggccacg      720
ggccggatct tgggtcggac aatgggtgag cgtttggtgg gttttctctgc ggaattaggc      780 ggaaagaacc ctcttattgt ggccaaggat gcagatctgg acaaggtgga agctgagctt      840
ccgcaggcgt gttttttccaa ctcggggcaa ttgtgtgtct ccactgaacg tatttatgtc      900
gaggaagacg tgtacgagga ggtgattgca cggtttagca aggcggcgaa agccatgtcc      960
attggtgccg gatttgagtg gaaatatgag atgggttcgt tgatcaatca ggcgcagctg     1020
gatcgggtga gcacctttgt tgatcaggct aaagctgcgg gcgccacggt gctgtgcggt     1080
ggcaagtcac gccctgatat tggtcccttc ttctatgagc ccacggtatt ggcggatgtc     1140
```

```
ccagagggca ccccactgct cacggaggaa gtcttcgggc cggtggtgtt catcgaaaag    1200
gtagccacac tggaagaagc cgtcgataag gcaaatggca cgccctacgg cctgaatgcg    1260
tccgtctttg gtcgtcgga accggcaat cttgttgcag gccagctgga agctggcggt      1320
atcggtatta atgatggcta cgccgcgacg tgggcgagcg tgtccacgcc tctgggtggc   1380
atgaagcagt cggggctggg gcaccgccat ggtgcggagg gaattacaaa atatgcggag    1440
atccgaaaca tcgcggagca cgctggatg tctatgcgtg ggccggccaa aatgccgcga     1500
aaggtgtact cagacaccgt ggccacagcg ctaaagctgg gcaaaatctt taaagttttg    1560
ccgtag                                                                1566
```

```
<210> SEQ ID NO 14
<211> LENGTH: 607
<212> TYPE: PRT
<213> ORGANISM: Ilyobacter polytropus
<220> FEATURE:
<221> NAME/KEY: MISC_FEATURE
<222> LOCATION: (1)..(607)
<223> OTHER INFORMATION: gdrA protein

<400> SEQUENCE: 14

Met Lys Ile Ile Val Gly Val Asp Ile Gly Asn Ala Thr Thr Glu Val
1               5                  10                  15

Ala Leu Ala Lys Val Asp Asn Ile Glu Cys Lys Phe Leu Ser Ser Ala
            20                  25                  30

Leu His Glu Thr Thr Gly Leu Lys Gly Thr Lys Asp Asn Val Leu Gly
        35                  40                  45

Ile Lys Arg Ala Ile Lys Lys Ala Met Lys Arg Ala Asp Leu Lys Asn
    50                  55                  60

Ala Asp Leu Ser Leu Ile Arg Ile Asn Glu Ala Thr Pro Val Ile Gly
65                  70                  75                  80

Asp Val Ser Met Glu Thr Ile Thr Glu Thr Ile Ile Thr Glu Ser Thr
                85                  90                  95

Met Ile Gly His Asn Pro Ser Thr Pro Gly Gly Ile Gly Leu Gly Ile
            100                 105                 110

Gly Glu Thr Ile Leu Phe Gln Glu Leu Gly Asn Phe Glu Asn Asp Lys
        115                 120                 125

Asp Tyr Ile Val Ile Val Glu Lys Ser Phe Ser Phe Leu Glu Val Ala
    130                 135                 140

His Arg Ile Asn Glu Ala Phe Lys Asn Gly Cys Lys Ile Lys Gly Ala
145                 150                 155                 160

Ile Ile Gln Lys Asp Asp Gly Val Leu Ile Asn Asn Arg Leu Ile Asn
                165                 170                 175

Lys Ile Pro Ile Val Asp Glu Val Leu Phe Val Lys Lys Val Pro Thr
            180                 185                 190

Gly Met Lys Ala Ala Val Glu Val Ala Pro Gln Gly Lys Ile Ile Glu
        195                 200                 205

Val Ile Ser Asn Pro Tyr Gly Ile Ala Thr Ile Phe Ser Leu Thr Ser
    210                 215                 220

Glu Glu Thr Lys Lys Ile Val Pro Ile Ser Lys Ala Leu Ile Gly Asn
225                 230                 235                 240

Arg Ser Gly Val Val Ile Lys Thr Pro His Gly Asp Val Lys Glu Lys
                245                 250                 255

Val Ile Pro Ala Gly Arg Ile Gln Ile Asp Gly Asn Tyr Arg Ser Lys
            260                 265                 270
```

```
Ser Val Asn Ile Glu Glu Gly Ser Lys Arg Ile Met Lys Ala Leu Gly
        275                 280                 285
Ser Ile Glu His Val Gln Asp Ile Asn Gly Glu Ser Gly Thr Asn Ile
        290                 295                 300
Gly Gly Met Leu Lys Asn Val Lys Ser Val Met Gly Asn Phe Thr Asn
305                 310                 315                 320
Glu Ser Ile Asp Asn Ile Lys Ile Lys Asp Ile Leu Ala Val Asp Thr
            325                 330                 335
Phe Val Pro Gln Lys Ile Lys Gly Gly Ile Ala Glu Glu Phe Val Phe
            340                 345                 350
Glu Asn Ala Val Gly Ile Ala Ala Met Val Asn Thr Lys Lys Asn Gln
        355                 360                 365
Met Ser Glu Val Ala Lys Glu Ile Glu Lys Glu Leu Gly Val Lys Val
        370                 375                 380
Glu Val Gly Gly Val Glu Ala Asp Met Ala Ile Thr Gly Ala Leu Thr
385                 390                 395                 400
Thr Pro Gly Thr Gly Thr Pro Leu Val Ile Val Asp Ile Gly Ala Gly
            405                 410                 415
Ser Thr Asp Ala Cys Ser Ile Asp Arg Tyr Gly Asn Lys Glu Leu Val
            420                 425                 430
His Leu Ala Gly Ala Gly Asn Met Thr Thr Leu Leu Ile Gln Lys Glu
        435                 440                 445
Leu Gly Ile Glu Asp Phe Asn Leu Ala Glu Asp Ile Lys Lys Tyr Pro
        450                 455                 460
Leu Ala Lys Val Glu Ser Leu Phe Tyr Ile Arg His Glu Asp Gly Asn
465                 470                 475                 480
Val Gln Phe Phe Glu Asn Ser Leu Ser Pro Lys Val Phe Ala Lys Asn
            485                 490                 495
Val Leu Ile Lys Glu Gly Glu Leu Ile Pro Ile Asp Leu Asp Met Ser
            500                 505                 510
Leu Glu Lys Ile Arg Ile Ile Arg Arg Ser Ala Lys Arg Lys Ile Phe
        515                 520                 525
Ile Thr Asn Val Leu Arg Ser Leu Arg Lys Val Ser His Thr Lys Asn
        530                 535                 540
Ile Arg Asp Phe Glu Phe Val Ile Val Gly Gly Ser Ala Leu Asp
545                 550                 555                 560
Phe Glu Ile Ser Gln Met Ile Thr Glu Ala Leu Ser Glu Tyr Gly Ile
            565                 570                 575
Val Ala Gly Cys Gly Asn Ile Arg Gly Thr Glu Gly Pro Arg Asn Ala
            580                 585                 590
Val Ala Thr Gly Leu Val Met Gly Val Asn Asp Gly Gln Gln Ala
        595                 600                 605

<210> SEQ ID NO 15
<211> LENGTH: 107
<212> TYPE: PRT
<213> ORGANISM: Ilyobacter polytropus
<220> FEATURE:
<221> NAME/KEY: MISC_FEATURE
<222> LOCATION: (1)..(107)
<223> OTHER INFORMATION: gdrB

<400> SEQUENCE: 15

Met Asp Asn Arg Pro Asn Ile Thr Leu Phe Cys Ser Asp Asn Ile Asp
1               5                   10                  15

Arg Glu Tyr Ile Asn Glu Ile Leu Trp Gly Ile Glu Glu Glu Glu Ile
```

|   |   |   |   | 20  |   |   |   | 25  |   |   |   | 30  |   |
|---|---|---|---|---|---|---|---|---|---|---|---|---|---|
Pro | Tyr | Leu | Leu | Lys | Ile | Val | Pro | Ser | Lys | Glu | Val | Lys | Glu | Asn
|   |   |   | 35 |   |   |   | 40 |   |   |   | 45 |   |   |

Tyr Val Ser Gly Thr Leu Glu Ile Gly Ile Gly Val Leu Glu Asn Gly
        50              55              60

Asp Ala Leu Leu Thr Thr Arg Lys Tyr Asp Lys Glu Tyr Ile Gln Lys
 65              70              75              80

Ala Asn Ile Phe Val Glu Lys Asn Lys Leu Arg Asp Leu Gly Ser Asn
                 85              90              95

Gly Ala Arg Leu Val Lys Gly Leu Pro Leu Arg
            100             105

<210> SEQ ID NO 16
<211> LENGTH: 1824
<212> TYPE: DNA
<213> ORGANISM: Ilyobacter polytropus
<220> FEATURE:
<221> NAME/KEY: gene
<222> LOCATION: (1)..(1824)
<223> OTHER INFORMATION: gdrA gene

<400> SEQUENCE: 16
atgaagatca tagtgggtgt agatattgga aatgctacaa cagaagtagc tttggcaaag     60
gtagacaata tagaatgtaa gttttttatcc agtgccttac atgaaacaac aggtttaaaa    120
ggtactaaag ataatgtttt gggaataaaa agagccatta agaaggcaat gaaaagagct    180
gatttaaaaa atgcagattt atctttaatc aggataaatg aagctactcc tgttatagga    240
gacgtttcta tggaaactat aacagaaaca ataattacag agtctactat gattggacat    300
aacccttcaa ctcctggggg aataggtctt gggataggag aaacaatcct attccaagag    360
cttggaaatt ttgaaaatga taagattac atagtaatag tggaaaaaag tttcagcttc    420
ttagaggtag ctcacagaat caatgaagct tttaaaaatg gatgcaaaat aaagggtgct    480
attattcaaa aagatgatgg ggttctcata ataacagac tcataaataa aatccccata    540
gttgatgagg tacttttttgt taaaaaagta cctacaggga tgaaggctgc tgtagaagta    600
gctccacagg gaaaaataat agaggttatt tcaaatccat atggcattgc cacaattttt    660
tccctcactt cagaagagac taaaaaaata gttcctatttt ctaaagcact tataggcaac    720
aggtctggag tagttatcaa gacacctcac ggagatgtaa agagaaggt tatccctgct    780 ggaaggatac agattgacgg aaactacagg tcaaaaagtg taaatataga agagggttcc    840
aaaagaataa tgaaagccct gggaagtatt gagcatgtcc aagatataaa tggagaatct    900
ggaaccaata tcggaggaat gctaaaaaat gtaaaagtg taatgggaa tttcaccaat    960 gagtccattg taatataaa aataaaagac atattggcag tagataccctt tgtcccacaa   1020 aagataaagg ggaattgc agaagaattt gtatttgaaa atgctgtagg aatagctgca   1080
atggtaaata ccaaaaaaaa tcaaatgtcc gaagtagcga aagagattga aaagaactg   1140 ggagtaaaag tagaagtagg aggagtagag gcagatatgg ctataaccgg tgctctaact   1200
actccaggca caggaacacc tctggtaatt gtagatatag gagcaggttc gacagatgca   1260
tgttccattg acagatatgg aaataaagaa ctggttcatc tggccggagc tggtaatatg   1320
acaacacttc ttattcaaaa agagctgggt atagaggatt taatcttgc tgaagatata   1380 aaaaaatatc tctggcaaa agtagaatct ctatttttata taagcacgga ggatggaaat   1440
gttcaatttt ttgaaaactc tctttctccg aaagtatttg ctaaaaatgt ccttataaaa   1500

```
gaaggtgaac ttattccaat cgaccttgat atgtctctgg aaaaaatcag aattatcaga    1560
aggtctgcca aaagaaaaat ttttataacc aatgtactta gatcattaag gaaagtttct    1620
catacaaaaa atattaggga ttttgaattt gtagttattg ttggaggatc tgcattggat    1680
tttgaaatat ctcagatgat aactgaagct ttatctgagt atggaatagt agcaggatgc    1740
ggaaatataa gaggaacaga gggccctaga aatgctgtag ccactggact tgtaatgggg    1800
gtgaatgatg acaacaggc ctaa                                            1824
```

<210> SEQ ID NO 17
<211> LENGTH: 324
<212> TYPE: DNA
<213> ORGANISM: Ilyobacter polytropus
<220> FEATURE:
<221> NAME/KEY: gene
<222> LOCATION: (1)..(324)
<223> OTHER INFORMATION: gdrB gene

<400> SEQUENCE: 17

```
atggacaaca ggcctaatat aacattattt tgctcagata atattgacag gaatatatt     60 aatgaaattt tgtggggtat agaggaggaa gagataccat atcttctgaa aattgtacct    120
tctaaagaag ttgtcaaaga aaattatgtt tcaggaactc tagagatagg tatcggagta    180
ttagaaaatg gcgacgccct tctaacaaca aggaagtacg ataaggaata tatacaaaag    240
gcaaacattt ttgtagaaaa aaataaattg agagatttag gaagcaacgg agcaagactt    300
gtaaagggtc tgccacttag ataa                                           324
```

<210> SEQ ID NO 18
<211> LENGTH: 607
<212> TYPE: PRT
<213> ORGANISM: Klebsiella pneumoniae
<220> FEATURE:
<221> NAME/KEY: MISC_FEATURE
<222> LOCATION: (1)..(607)
<223> OTHER INFORMATION: gdrA protein

<400> SEQUENCE: 18

```
Met Pro Leu Ile Ala Gly Ile Asp Ile Gly Asn Ala Thr Thr Glu Val
1               5                   10                  15

Ala Leu Ala Ser Asp Asp Pro Gln Ala Arg Ala Phe Val Ala Ser Gly
            20                  25                  30

Ile Val Ala Thr Thr Gly Met Lys Gly Thr Arg Asp Asn Ile Ala Gly
        35                  40                  45

Thr Leu Ala Ala Leu Glu Gln Ala Leu Ala Lys Thr Pro Trp Ser Val
    50                  55                  60

Ser Asp Val Ser Arg Ile Tyr Leu Asn Glu Ala Ala Pro Val Ile Gly
65                  70                  75                  80

Asp Val Ala Met Glu Thr Ile Thr Glu Thr Ile Ile Thr Glu Ser Thr
                85                  90                  95

Met Ile Gly His Asn Pro Gln Thr Pro Gly Gly Val Gly Val Gly Val
            100                 105                 110

Gly Thr Thr Ile Ala Leu Gly Arg Leu Ala Thr Leu Pro Ala Ala Gln
        115                 120                 125

Tyr Ala Glu Gly Trp Ile Val Leu Ile Asp Asp Ala Val Asp Phe Leu
    130                 135                 140

Asp Ala Val Trp Trp Leu Asn Glu Ala Leu Asp Arg Gly Ile Asn Val
145                 150                 155                 160

Val Ala Ala Ile Leu Lys Lys Asp Asp Gly Val Leu Val Asn Asn Arg
```

```
                165                 170                 175
Leu Arg Lys Thr Leu Pro Val Val Asp Glu Val Thr Leu Leu Glu Gln
            180                 185                 190

Val Pro Glu Gly Val Met Ala Ala Val Glu Val Ala Ala Pro Gly Gln
            195                 200                 205

Val Val Arg Ile Leu Ser Asn Pro Tyr Gly Ile Ala Thr Phe Phe Gly
            210                 215                 220

Leu Ser Pro Glu Glu Thr Gln Ala Ile Val Pro Ile Ala Arg Ala Leu
225                 230                 235                 240

Ile Gly Asn Arg Ser Ala Val Val Leu Lys Thr Pro Gln Gly Asp Val
                245                 250                 255

Gln Ser Arg Val Ile Pro Ala Gly Asn Leu Tyr Ile Ser Gly Glu Lys
            260                 265                 270

Arg Arg Gly Glu Ala Asp Val Ala Glu Gly Ala Glu Ala Ile Met Gln
            275                 280                 285

Ala Met Ser Ala Cys Ala Pro Val Arg Asp Ile Arg Gly Glu Pro Gly
            290                 295                 300

Thr His Ala Gly Gly Met Leu Glu Arg Val Arg Lys Val Met Ala Ser
305                 310                 315                 320

Leu Thr Asp His Glu Met Ser Ala Ile Tyr Ile Gln Asp Leu Leu Ala
                325                 330                 335

Val Asp Thr Phe Ile Pro Arg Lys Val Gln Gly Gly Met Ala Gly Glu
            340                 345                 350

Cys Ala Met Glu Asn Ala Val Gly Met Ala Ala Met Val Lys Ala Asp
            355                 360                 365

Arg Leu Gln Met Gln Val Ile Ala Arg Glu Leu Ser Ala Arg Leu Gln
            370                 375                 380

Thr Glu Val Val Val Gly Gly Val Glu Ala Asn Met Ala Ile Ala Gly
385                 390                 395                 400

Ala Leu Thr Thr Pro Gly Cys Ala Ala Pro Leu Ala Ile Leu Asp Leu
                405                 410                 415

Gly Ala Gly Ser Thr Asp Ala Ala Ile Val Asn Ala Glu Gly Gln Ile
            420                 425                 430

Thr Ala Val His Leu Ala Gly Ala Gly Asn Met Val Ser Leu Leu Ile
            435                 440                 445

Lys Thr Glu Leu Gly Leu Glu Asp Leu Ser Leu Ala Glu Ala Ile Lys
            450                 455                 460

Lys Tyr Pro Leu Ala Lys Val Glu Ser Leu Phe Ser Ile Arg His Glu
465                 470                 475                 480

Asn Gly Ala Val Glu Phe Phe Arg Glu Ala Leu Ser Pro Ala Val Phe
                485                 490                 495

Ala Lys Val Val Tyr Ile Lys Glu Gly Glu Leu Val Pro Ile Asp Asn
            500                 505                 510

Ala Ser Pro Leu Glu Lys Ile Arg Leu Val Arg Arg Gln Ala Lys Glu
            515                 520                 525

Lys Val Phe Val Thr Asn Cys Leu Arg Ala Leu Arg Gln Val Ser Pro
            530                 535                 540

Gly Gly Ser Ile Arg Asp Ile Ala Phe Val Val Leu Val Gly Gly Ser
545                 550                 555                 560

Ser Leu Asp Phe Glu Ile Pro Gln Leu Ile Thr Glu Ala Leu Ser His
                565                 570                 575

Tyr Gly Val Val Ala Gly Gln Gly Asn Ile Arg Gly Thr Glu Gly Pro
            580                 585                 590
```

Arg Asn Ala Val Ala Thr Gly Leu Leu Leu Ala Gly Gln Ala Asn
        595                 600                 605

<210> SEQ ID NO 19
<211> LENGTH: 117
<212> TYPE: PRT
<213> ORGANISM: Klebsiella pneumoniae
<220> FEATURE:
<221> NAME/KEY: MISC_FEATURE
<222> LOCATION: (1)..(117)
<223> OTHER INFORMATION: gdrB protein

<400> SEQUENCE: 19

Met Ser Leu Ser Pro Pro Gly Val Arg Leu Phe Tyr Asp Pro Arg Gly
1               5                   10                  15

His His Ala Gly Ala Ile Asn Glu Leu Cys Trp Gly Leu Glu Glu Gln
            20                  25                  30

Gly Val Pro Cys Gln Thr Ile Thr Tyr Asp Gly Gly Asp Ala Ala
        35                  40                  45

Ala Leu Gly Ala Leu Ala Ala Arg Ser Ser Pro Leu Arg Val Gly Ile
    50                  55                  60

Gly Leu Ser Ala Ser Gly Glu Ile Ala Leu Thr His Ala Gln Leu Pro
65                  70                  75                  80

Ala Asp Ala Pro Leu Ala Thr Gly His Val Thr Asp Ser Asp His
                85                  90                  95

Leu Arg Thr Leu Gly Ala Asn Ala Gly Gln Leu Val Lys Val Leu Pro
            100                 105                 110

Leu Ser Glu Arg Asn
        115

<210> SEQ ID NO 20
<211> LENGTH: 1824
<212> TYPE: DNA
<213> ORGANISM: Klebsiella pneumoniae
<220> FEATURE:
<221> NAME/KEY: gene
<222> LOCATION: (1)..(1824)
<223> OTHER INFORMATION: gdrA gene

<400> SEQUENCE: 20
atgccgttaa tagccgggat tgatatcggc aacgccacca ccgaggtggc gctggcgtcc      60
gacgacccgc aggcgagggc gtttgttgcc agcgggatcg tcgcgacgac gggcatgaaa     120
gggacgcggg acaatatcgc cgggacccct gccgcgctgg agcaggccct ggcgaaaaca     180
ccgtggtcgg tgagcgatgt ctctcgcatc tatcttaacg aagccgcgcc ggtgattggc     240
gatgtggcga tggagaccat caccgagacc attatcaccg aatcgaccat gatcggtcat     300
aacccgcaga cgccgggcgg ggtgggcgtt ggcgtgggga cgactatcgc cctcggcgg     360 ctggcgacgc tgccggcggc gcagtatgcc gaggggtgga tcgtactgat tgacgacgcc     420
gtcgatttcc ttgacgccgt gtggtggctc aatgaggcgc tcgaccgggg atcaacgtg      480 gtggcggcga tcctcaaaaa ggacgacggc gtgctggtga caaccgcct gcgtaaaacc     540 ctgccggtgg tagatgaagt gacgctgctg agcaggtcc ccgaggggt aatgcggcg     600 gtggaagtgg ccgcgccggg ccaggtggtg cggatcctgt cgaatcccta cgggatcgcc     660
accttcttcg ggctaagccc ggaagagacc caggccatcg tccccatcgc ccgcgccctg     720
attggcaacc gttcagcggt ggtgctcaag acccgcagg gggatgtgca gtcgcgggtg     780
atcccggcgg gcaacctcta cattagcggc gaaaagcgcc gcggagaggc cgatgtcgcc     840

```
gagggcgcgg aagccatcat gcaggcgatg agcgcctgcg ctccggtacg cgacatccgc    900
ggcgaaccgg gcactcacgc cggcggcatg cttgagcggg tgcgcaaggt aatggcgtcc    960
ctgaccgacc atgagatgag cgcgatatac atccaggatc tgctggcggt ggatacgttt   1020
attccgcgca aggtgcaggg cgggatggcc ggcgagtgcg ccatggaaaa tgccgtcggg   1080
atggcggcga tggtgaaagc ggatcgtctg caaatgcagg ttatcgcccg cgaactgagc   1140
gcccgactgc agaccgaggt ggtggtgggc ggcgtggagg ccaacatggc catcgccggg   1200
gcgttaacca ctcccggctg tgcggcgccg ctggcgatcc tcgacctcgg cgccggctcg   1260
acggatgcgg cgatcgtcaa cgcggagggg cagataacgg cggtccatct cgccggggcg   1320
gggaatatgg tcagcctgtt gattaaaacc gagctgggcc tcgaggatct ttcgctggcg   1380
gaagcgataa aaaatacccc gctggccaaa gtggaaagcc tgttcagtat tcgtcacgag   1440
aatggcgcgg tggagttctt tcgggaagcc ctcagcccgg cggtgttcgc caaagtggtg   1500
tacatcaagg agggcgaact ggtgccgatc gataacgcca gcccgctgga aaaaattcgt   1560
ctcgtgcgcc ggcaggcgaa agagaaagtg tttgtcacca actgcctgcg cgcgctgcgc   1620
caggtctcac ccggcggttc cattcgcgat atcgcctttg tggtgctggt gggcggctca   1680
tcgctggact ttgagatccc gcagcttatc acggaagcct tgtcgcacta tggcgtggtc   1740
gccgggcagg gcaatattcg gggaacagaa gggccgcgca acgcggtcgc caccgggctg   1800
ctactggccg gtcaggcgaa ttaa                                          1824

<210> SEQ ID NO 21
<211> LENGTH: 354
<212> TYPE: DNA
<213> ORGANISM: Klebsiella pneumoniae
<220> FEATURE:
<221> NAME/KEY: gene
<222> LOCATION: (1)..(354)
<223> OTHER INFORMATION: gdrB gene

<400> SEQUENCE: 21
atgtcgcttt caccgccagg cgtacgcctg ttttacgatc cgcgcgggca ccatgccggc     60
gccatcaatg agctgtgctg ggggctggag gagcaggggg tccccctgcca gaccataacc    120 tatgacggag gcggtgacgc cgctgcgctg ggcgccctgg cggccagaag ctcgcccctg    180
cgggtgggta ttgggctcag cgcgtccggc gagatagccc tcactcatgc ccagctgccg    240
gcggacgcgc cgctggctac cggacacgtc accgatagcg acgatcatct gcgtacgctc    300
ggcgccaacg ccgggcagct ggttaaagtc ctgccgttaa gtgagagaaa ctga          354

<210> SEQ ID NO 22
<211> LENGTH: 258
<212> TYPE: PRT
<213> ORGANISM: Megasphaera elsdenii
<220> FEATURE:
<221> NAME/KEY: MISC_FEATURE
<222> LOCATION: (1)..(258)
<223> OTHER INFORMATION: ATCC17753 pct protein

<400> SEQUENCE: 22

Met Ser Asp Glu Thr Leu Val Leu Ser Thr Ile Glu Gly Pro Val Ala
1               5                   10                  15

Ile Leu Thr Leu Asn Arg Pro Gln Ala Leu Asn Ala Leu Ser Pro Ala
            20                  25                  30

Leu Ile Asp Ala Leu Ile Arg His Leu Glu His Cys Asp Asn Asp Asp
        35                  40                  45
```

Thr Ile Arg Val Ile Ile Thr Gly Ala Gly Arg Ala Phe Ala Ala
 50                  55                  60

Gly Ala Asp Ile Lys Ala Met Ala Asp Ala Thr Pro Ile Asp Met Leu
 65                  70                  75                  80

Thr Thr Asp Met Ile Ala Arg Trp Ala Arg Ile Ala Ala Val Arg Lys
                 85                  90                  95

Pro Val Ile Ala Ala Val Asn Gly Phe Ala Leu Gly Gly Gly Cys Glu
                100                 105                 110

Leu Ala Met Met Cys Asp Ile Ile Leu Ala Ser Glu Thr Ala Gln Phe
            115                 120                 125

Gly Gln Pro Glu Ile Asn Ile Gly Ile Ile Pro Gly Ala Gly Gly Thr
        130                 135                 140

Gln Arg Leu Thr Arg Ala Ile Gly Pro Tyr Arg Ala Met Glu Met Val
145                 150                 155                 160

Leu Thr Gly Ala Thr Ile Ser Ala Gln Glu Ala Tyr Ala Tyr Gly Leu
                165                 170                 175

Val Asn Arg Val Cys Pro Pro Asp Ser Leu Leu Asp Glu Ala Arg Arg
            180                 185                 190

Leu Ala Gln Thr Ile Ala Ala Lys Pro Pro Leu Ala Val Arg Leu Ala
        195                 200                 205

Lys Glu Ala Val Arg Ala Ala Glu Thr Thr Val Arg Glu Gly Leu
210                 215                 220

Ala Ile Glu Leu Arg Asn Phe Tyr Leu Leu Phe Ala Ser Ala Asp Gln
225                 230                 235                 240

Lys Glu Gly Met Arg Ala Phe Ile Glu Lys Arg Thr Ala Asn Phe Ser
                245                 250                 255

Gly Arg

<210> SEQ ID NO 23
<211> LENGTH: 777
<212> TYPE: DNA
<213> ORGANISM: Megasphaera elsdenii
<220> FEATURE:
<221> NAME/KEY: MISC_FEATURE
<222> LOCATION: (1)..(777)
<223> OTHER INFORMATION: ATCC17753

<400> SEQUENCE: 23
atgagcgatg aaacgcttgt gctcagcact atcgaaggcc ccgttgcaat ccttacgctc      60
aatcgaccac aagcactcaa tgcccttagc cctgccctca tcgacgcact catccgccat     120
cttgagcatt gcgataacga cgatacgatc cgggtgatca ttatcaccgg cgccggtcgc     180
gcctttgccg ccggcgccga catcaaggcg atggccgatg cgacgccgat cgatatgctt     240
acaaccgata tgattgcccg ctgggcgcgg attgcggcgg tgcgcaaacc cgtgatcgca     300
gccgtgaacg gatttgccct cggtggtggc tgcgagttgg ctatgatgtg tgacatcatt     360
cttgccagtg aaacagccca attcggtcaa cccgaaatca acatcggcat tatccccggc     420
gccggtggca cccaacgcct gacccgcgca attgcccat accgtgcaat ggagatggtc     480
ttaaccggtg ctaccatcag tgcccaagaa gcttacgcct acggcctggt gaatcgggta     540
tgcccacccg atagcctgct tgatgaagcc cgccggttgg cccagaccat tgcagccaag     600
ccgccgctcg ctgtgcgttt agccaaggaa gccgtgcgcg ctgcggctga aacgaccgtg     660
cgtgaagggt tagccattga attgcgtaac ttttatctgc tctttgccag tgccgatcag     720
aaagagggca tgcgagcctt tatcgaaaag cgtacagcca acttcagtgg tcgctaa        777

<210> SEQ ID NO 24
<211> LENGTH: 132
<212> TYPE: PRT
<213> ORGANISM: Escherichia coli
<220> FEATURE:
<221> NAME/KEY: MISC_FEATURE
<222> LOCATION: (1)..(132)
<223> OTHER INFORMATION: K yciA protein

<400> SEQUENCE: 24

```
Met Ser Thr Thr His Asn Val Pro Gln Gly Asp Leu Val Leu Arg Thr
1               5                   10                  15

Leu Ala Met Pro Ala Asp Thr Asn Ala Asn Gly Asp Ile Phe Gly Gly
            20                  25                  30

Trp Leu Met Ser Gln Met Asp Ile Gly Gly Ala Ile Leu Ala Lys Glu
        35                  40                  45

Ile Ala His Gly Arg Val Val Thr Val Arg Val Glu Gly Met Thr Phe
    50                  55                  60

Leu Arg Pro Val Ala Val Gly Asp Val Val Cys Cys Tyr Ala Arg Cys
65                  70                  75                  80

Val Gln Lys Gly Thr Thr Ser Val Ser Ile Asn Ile Glu Val Trp Val
                85                  90                  95

Lys Lys Val Ala Ser Glu Pro Ile Gly Gln Arg Tyr Lys Ala Thr Glu
            100                 105                 110

Ala Leu Phe Lys Tyr Val Ala Val Asp Pro Glu Gly Lys Pro Arg Ala
        115                 120                 125

Leu Pro Val Glu
    130
```

<210> SEQ ID NO 25
<211> LENGTH: 399
<212> TYPE: DNA
<213> ORGANISM: Escherichia coli
<220> FEATURE:
<221> NAME/KEY: gene
<222> LOCATION: (1)..(399)
<223> OTHER INFORMATION: K yciA gene

<400> SEQUENCE: 25

```
atgtctacaa cacataacgt ccctcagggc gatcttgttt tacgtacttt agccatgccc    60
gccgatacca atgccaatgg tgacatcttt ggtggttggt taatgtcaca aatggatatt   120
ggcggcgcta ttctggcaaa agaaattgcc cacggtcgcg tagtgactgt gcgggttgaa   180
ggaatgactt tcttacggcc ggttgcggtc ggcgatgtgg tgtgctgcta tgcacgctgt   240
gtccagaaag ggacgacatc ggtcagcatt aatattgaag tgtgggtgaa aaaagtagcg   300
tctgaaccaa ttgggcaacg ctataaagcg acagaagcat tatttaagta tgtcgcggtt   360
gatcctgaag gaaaaccctcg cgccttacct gttgagtaa                         399
```

<210> SEQ ID NO 26
<211> LENGTH: 262
<212> TYPE: PRT
<213> ORGANISM: Chloroflexus aurantiacus
<220> FEATURE:
<221> NAME/KEY: MISC_FEATURE
<222> LOCATION: (1)..(262)
<223> OTHER INFORMATION: hpd protein

<400> SEQUENCE: 26

Met Asp Phe Asn Asn Ile Ile Leu Glu Lys Glu Glu Lys Ile Ala Val

|     |     |     |     |     |     |     |     |     |     |     |     |     |     |     |     |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Val | Thr | Ile | Asn | Arg | Pro | Lys | Ala | Leu | Asn | Ala | Leu | Asn | Ser | Glu | Thr |
|     |     |     | 20  |     |     |     |     | 25  |     |     |     |     | 30  |     |     |
| Leu | Thr | Glu | Leu | Asp | Ser | Val | Ile | Asp | Glu | Ile | Asp | Lys | Asp | Asn | Glu |
|     |     | 35  |     |     |     |     | 40  |     |     |     |     | 45  |     |     |     |
| Ile | Leu | Ala | Val | Val | Leu | Thr | Gly | Ala | Gly | Lys | Ser | Phe | Val | Ala | Gly |
|     | 50  |     |     |     |     | 55  |     |     |     |     | 60  |     |     |     |     |
| Ala | Asp | Ile | Ser | Glu | Met | Lys | Asp | Met | Asn | Val | Val | Glu | Gly | Arg | Lys |
| 65  |     |     |     |     | 70  |     |     |     |     | 75  |     |     |     |     | 80  |
| Phe | Gly | Ile | Leu | Gly | Asn | Lys | Val | Phe | Arg | Lys | Leu | Glu | Asn | Leu | Glu |
|     |     |     |     | 85  |     |     |     |     | 90  |     |     |     |     | 95  |     |
| Lys | Pro | Val | Ile | Ala | Ala | Leu | Asn | Gly | Phe | Thr | Leu | Gly | Gly | Gly | Cys |
|     |     |     | 100 |     |     |     |     | 105 |     |     |     |     | 110 |     |     |
| Glu | Ile | Ala | Met | Ser | Cys | Asp | Ile | Arg | Ile | Ala | Ser | Thr | Lys | Ala | Lys |
|     |     | 115 |     |     |     |     | 120 |     |     |     |     | 125 |     |     |     |
| Phe | Gly | Gln | Pro | Glu | Val | Gln | Leu | Gly | Ile | Thr | Pro | Gly | Phe | Gly | Gly |
|     | 130 |     |     |     |     | 135 |     |     |     |     | 140 |     |     |     |     |
| Thr | Gln | Arg | Leu | Ala | Arg | Leu | Ile | Gly | Pro | Gly | Ala | Ala | Lys | Glu | Leu |
| 145 |     |     |     |     | 150 |     |     |     |     | 155 |     |     |     |     | 160 |
| Ile | Tyr | Thr | Gly | Lys | Ile | Ile | Asn | Ala | Glu | Glu | Ala | Tyr | Arg | Leu | Gly |
|     |     |     |     | 165 |     |     |     |     | 170 |     |     |     |     | 175 |     |
| Leu | Val | Asn | Arg | Val | Ile | Glu | Pro | Glu | Thr | Leu | Leu | Asp | Glu | Ala | Lys |
|     |     |     | 180 |     |     |     |     | 185 |     |     |     |     | 190 |     |     |
| Gln | Leu | Ala | Asn | Thr | Ile | Ala | Ala | Asn | Ala | Pro | Ile | Ala | Val | Lys | Leu |
|     |     | 195 |     |     |     |     | 200 |     |     |     |     | 205 |     |     |     |
| Ala | Lys | Ser | Ala | Ile | Asn | Arg | Gly | Ile | Gln | Thr | Asp | Ile | Asp | Thr | Gly |
|     | 210 |     |     |     |     | 215 |     |     |     |     | 220 |     |     |     |     |
| Val | Ser | Ile | Glu | Ser | Glu | Val | Phe | Gly | Ala | Cys | Phe | Ser | Thr | Glu | Asp |
| 225 |     |     |     |     | 230 |     |     |     |     | 235 |     |     |     |     | 240 |
| Gln | Lys | Glu | Gly | Met | Asn | Thr | Phe | Leu | Asn | Asp | Lys | Lys | Tyr | Leu | Thr |
|     |     |     |     | 245 |     |     |     |     | 250 |     |     |     |     | 255 |     |
| Gly | Asn | Phe | Lys | Asn | Lys |     |     |     |     |     |     |     |     |     |     |
|     |     |     |     | 260 |     |     |     |     |     |     |     |     |     |     |     |

<210> SEQ ID NO 27
<211> LENGTH: 789
<212> TYPE: DNA
<213> ORGANISM: Chloroflexus aurantiacus
<220> FEATURE:
<221> NAME/KEY: gene
<222> LOCATION: (1)..(789)
<223> OTHER INFORMATION: hpd gene

<400> SEQUENCE: 27

```
atggatttta taatattat ccttgaaaaa gaggaaaaaa ttgccgtagt tacaattaat      60
agacctaaag ctcttaatgc tttgaacagt gaaacgttaa ctgagcttga ttctgtaatt    120
gatgaaattg acaaagataa tgaaatttta gcagtggtat taacgggagc gggaaaatcc    180
ttcgtagctg gagccgatat atcagaaatg aaagacatga atgtagtaga aggaagaaaa    240
tttggaatac taggtaataa ggtgttcaga aacttgaaaa attagaaaaa gccagtaata    300
gcagccctta atggatttac attgggtggt ggttgtgaaa ttgctatgtc ttgcgatata    360
agaatagctt ctactaaggc aaaatttgga cagccagagg tacagcttgg ataactcca    420 ggttttggcg gtactcaaag attagctaga ttaataggcc caggagctgc aaaggaactt    480
atatatactg gaaaaattat aaatgctgaa gaggcctata gattaggact tgttaataga    540
```

```
gttatagaac cagaaacttt attagatgaa gcaaaacaat tggcaaatac tatagcagcc    600
aatgcaccta tagctgttaa gttggctaaa tcagcaataa atagaggaat tcaaactgat    660
attgatacag gtgtgtcaat tgaatcagaa gtatttggag cttgtttctc tacagaagat    720 caaaagaag gtatgaatac attcttgaat gataaaaaat atttaactgg taattttaag    780
aataaataa                                                             789
```

```
<210> SEQ ID NO 28
<211> LENGTH: 35
<212> TYPE: DNA
<213> ORGANISM: Artificial Sequence
<220> FEATURE:
<223> OTHER INFORMATION: Synthetic (primer: hdpA_F)

<400> SEQUENCE: 28
aaaccatggc agtgaacatt tcatatctga ccgac                                35

<210> SEQ ID NO 29
<211> LENGTH: 31
<212> TYPE: DNA
<213> ORGANISM: Artificial Sequence
<220> FEATURE:
<223> OTHER INFORMATION: Synthetic (primer: hdpA_R)

<400> SEQUENCE: 29
aaaggatccc tagtcagtga actgctgctc a                                    31

<210> SEQ ID NO 30
<211> LENGTH: 32
<212> TYPE: DNA
<213> ORGANISM: Artificial Sequence
<220> FEATURE:
<223> OTHER INFORMATION: Synthetic (primer: gldA_F)

<400> SEQUENCE: 30
aaacatatgg accgcattat tcaatcaccg gg                                   32

<210> SEQ ID NO 31
<211> LENGTH: 37
<212> TYPE: DNA
<213> ORGANISM: Artificial Sequence
<220> FEATURE:
<223> OTHER INFORMATION: Synthetic (primer: gldA_R)

<400> SEQUENCE: 31
aaactcgagt tattcccact cttgcaggaa acgctga                              37

<210> SEQ ID NO 32
<211> LENGTH: 32
<212> TYPE: DNA
<213> ORGANISM: Artificial Sequence
<220> FEATURE:
<223> OTHER INFORMATION: Synthetic (primer: dhaB123_F)

<400> SEQUENCE: 32
tcatgaaatc aaaagattt gaagtattga ag                                    32

<210> SEQ ID NO 33
<211> LENGTH: 36
<212> TYPE: DNA
<213> ORGANISM: Artificial Sequence
<220> FEATURE:
<223> OTHER INFORMATION: Synthetic (primer: dhaB123_R)
```

<400> SEQUENCE: 33

```
ggatccctaa tcttttctaa gttgacctct ttgttc                                    36
```

<210> SEQ ID NO 34
<211> LENGTH: 30
<212> TYPE: DNA
<213> ORGANISM: Artificial Sequence
<220> FEATURE:
<223> OTHER INFORMATION: Synthetic (primer: gdrAB_F)

<400> SEQUENCE: 34

```
ggatccaaag gttcggggat agttatgaag                                            30
```

<210> SEQ ID NO 35
<211> LENGTH: 33
<212> TYPE: DNA
<213> ORGANISM: Artificial Sequence
<220> FEATURE:
<223> OTHER INFORMATION: Synthetic (primer: gdrAB_R)

<400> SEQUENCE: 35

```
gagctcttat ctaagtggca gaccctttac aag                                       33
```

<210> SEQ ID NO 36
<211> LENGTH: 1194
<212> TYPE: DNA
<213> ORGANISM: Ralstonia eutropha
<220> FEATURE:
<221> NAME/KEY: gene
<222> LOCATION: (1)..(1194)
<223> OTHER INFORMATION: Cupriavidus necator succinate semialdehyde
      dehydrogenase (SSADH) protein gene: gabD

<400> SEQUENCE: 36

```
atgcacgccg ccacgcaagc catcctcacc ttcaaccatg gccgcgatcc cgagcggctg         60
acccgcaagc ttgcggcgat cgccgcggac ccgtttgcct tctttcgcgg caccaaccat        120
ctctatgccg catcgctgcg cgatgaggcg gcaatgtgca atgcgcccat cacctacgtc        180
tgcggcgatc tgcacctgga gaacttcggc agcttcaagg cgacaacgg gctggtctat         240
ttcgacctga cgactttga cgatgccctg gtcgcgccgc ttacggtgga tgtggtccgg         300
atgctgtcga gcgtgctggt ggccgccggc cagctgggcc tttccgaggc cggcgccatg        360
cgcgcctgcg aggccatgct gtccacctat gccgccgtgc tgcagacagg caagcctcgc        420
tggctcgagc gtgccacggc ggtcggcatg gtggccaccc tgctgcgccg ggtcaagggc        480
cgcaagcgcg cgcgcgctgct ggccgagctc accacgctgc gcaagggcaa acggcgcctg      540
gtatgcaacg ccgccatgc gctgccggcg acaagccgg cccgtgagcg cgctcgcgcg          600
atccttgcgg cctactcgaa gcagggccac catggccacc gcctgcccct cgacgatgcc        660
gcgcggcgcg tggcgggcat tgcagcctc gggctggaac gctatatggt gctggcgcgg         720
gacgaactga gcggcatgca gcgactggtc gacatcaagc gcgccgcgcc gagtccatgg        780
caggacctgc ccagcctgtc cctgccaccc tggggcagcg atgcaaggcg ggtggcggcg        840
gtgcagcaag tcatgcaggc ggcttcgccg gcgctgctgt cggctgtcga catgggcaag        900
gcttcctatc tggtcaagag cctgcagcca actgccgacc gcgtcgacct ggcgcattgc        960
agcaactttg cagcgctacg cgagttgctg ggcaccatgg cgcatgccgc ggcatgggcg       1020
catctgcgtg gctgcgggca ccaggccgcg gaccggatcg agcagctgca ggcgtttgcc       1080
ggcggcaccc gctggcgcac cggcgtcctg cggctggcac ggcatggctg cgcggtgtcg       1140
```
gtggtgcagt ggaaggcgta tgcggacgat taccgcgagg cgcggggagg gtga         1194

<210> SEQ ID NO 37
<211> LENGTH: 28
<212> TYPE: DNA
<213> ORGANISM: Artificial Sequence
<220> FEATURE:
<223> OTHER INFORMATION: Synthetic (primer: gabD_F)

<400> SEQUENCE: 37
aaagctagca tgtaccagga tctcgccc                                       28

<210> SEQ ID NO 38
<211> LENGTH: 30
<212> TYPE: DNA
<213> ORGANISM: Artificial Sequence
<220> FEATURE:
<223> OTHER INFORMATION: Synthetic (primer: gabD_R)

<400> SEQUENCE: 38
aatggtacct caggcctggg tgatgaactt                                     30

<210> SEQ ID NO 39
<211> LENGTH: 33
<212> TYPE: DNA
<213> ORGANISM: Artificial Sequence
<220> FEATURE:
<223> OTHER INFORMATION: Synthetic (primer: pct_F)

<400> SEQUENCE: 39
aaaggatcca atgagaaaag tagaaatcat tac                                 33

<210> SEQ ID NO 40
<211> LENGTH: 28
<212> TYPE: DNA
<213> ORGANISM: Artificial Sequence
<220> FEATURE:
<223> OTHER INFORMATION: Synthetic (primer: pct_R)

<400> SEQUENCE: 40
aaagagctcg gcgaagttga cgataatg                                       28

<210> SEQ ID NO 41
<211> LENGTH: 44
<212> TYPE: DNA
<213> ORGANISM: Artificial Sequence
<220> FEATURE:
<223> OTHER INFORMATION: Synthetic (primer: yciA_F)

<400> SEQUENCE: 41
aaagagctca atgtctacaa cacataacgt ccctcagggc gatc                     44

<210> SEQ ID NO 42
<211> LENGTH: 37
<212> TYPE: DNA
<213> ORGANISM: Artificial Sequence
<220> FEATURE:
<223> OTHER INFORMATION: Synthetic (primer: yciA_R)

<400> SEQUENCE: 42
aagcttttac tcaacaggta aggcgcgagg ttttcct                             37

<210> SEQ ID NO 43
<211> LENGTH: 26
<212> TYPE: DNA
<213> ORGANISM: Artificial Sequence
<220> FEATURE:
<223> OTHER INFORMATION: Synthetic (primer: hpdF)

<400> SEQUENCE: 43
gggaattcca tatgatcgac actgcg                                              26

<210> SEQ ID NO 44
<211> LENGTH: 30
<212> TYPE: DNA
<213> ORGANISM: Artificial Sequence
<220> FEATURE:
<223> OTHER INFORMATION: Synthetic (primer: hpdR)

<400> SEQUENCE: 44
cgaactcgag aacgataatc ggctcagcac                                          30

<210> SEQ ID NO 45
<211> LENGTH: 554
<212> TYPE: PRT
<213> ORGANISM: Ilyobacter polytropus
<220> FEATURE:
<221> NAME/KEY: MISC_FEATURE
<222> LOCATION: (1)..(554)
<223> OTHER INFORMATION: DhaB1 protein

<400> SEQUENCE: 45

Met Lys Ser Lys Arg Phe Glu Val Leu Lys Glu Arg Pro Val Asn Lys
1               5                   10                  15

Asp Gly Phe Ile Ser Glu Trp Ile Glu Glu Gly Leu Ile Ala Met Glu
            20                  25                  30

Ser Pro Asn Asp Pro Asn Pro Ser Leu Lys Ile Glu Asn Gly Gln Ile
        35                  40                  45

Thr Glu Leu Asp Gly Lys Ser Arg Glu Glu Phe Asp Met Ile Asp Arg
    50                  55                  60

Phe Ile Ala Asp Tyr Ala Ile Asn Met Glu Asn Ala Glu Lys Ala Met
65                  70                  75                  80

Lys Met Ser Ser Met Glu Ile Ser Lys Lys Leu Val Asp Ile Asn Val
                85                  90                  95

Ser Arg Asp Glu Val Leu Glu Ile Thr Thr Gly Ile Thr Pro Ala Lys
            100                 105                 110

Ile Ile Lys Val Met Glu His Met Asn Val Val Glu Met Met Met Ala
        115                 120                 125

Val Gln Lys Met Arg Ala Arg Lys Thr Pro Ser Asn Gln Cys His Val
    130                 135                 140

Thr Asn Leu Arg Asp Asn Pro Val Leu Ile Ala Ala Asp Ala Ala Glu
145                 150                 155                 160

Ala Ser Val Arg Gly Phe Asp Glu Gln Glu Thr Thr Ile Gly Ile Val
                165                 170                 175

Arg Tyr Ala Pro Phe Asn Ala Ile Ser Ile Phe Val Gly Ser Gln Val
            180                 185                 190

Gly Arg Gly Gly Ile Leu Thr Gln Cys Ser Val Glu Glu Ala Thr Glu
        195                 200                 205

Leu Glu Leu Gly Met Lys Gly Phe Thr Ser Tyr Ala Glu Thr Val Ser
    210                 215                 220

Val Tyr Gly Thr Glu Gln Val Phe Ile Asp Gly Asp Asp Thr Pro Trp
225                 230                 235                 240

Ser Lys Ala Phe Leu Ala Ser Ala Tyr Ala Ser Arg Gly Leu Lys Met
                245                 250                 255

```
Arg Phe Thr Ser Gly Thr Gly Ser Glu Ala Leu Met Gly Asn Ala Glu
            260                 265                 270

Gly Lys Ser Met Leu Tyr Leu Glu Ala Arg Cys Ile Tyr Val Thr Arg
        275                 280                 285

Gly Ser Gly Val Gln Gly Leu Gln Asn Gly Ser Val Ser Cys Ile Gly
    290                 295                 300

Met Pro Gly Ser Leu Pro Gly Gly Ile Arg Ala Val Leu Ala Glu Asn
305                 310                 315                 320

Leu Ile Ala Met Leu Leu Asp Leu Glu Cys Ala Ser Ala Asn Asp Gln
                325                 330                 335

Thr Phe Ser His Ser Glu Tyr Arg Arg Thr Ala Arg Thr Leu Met Gln
            340                 345                 350

Met Leu Pro Gly Thr Asp Phe Ile Phe Ser Gly Tyr Ser Ala Val Pro
        355                 360                 365

Asn Cys Asp Asn Met Phe Ala Gly Ser Asn Phe Asp Ala Glu Asp Phe
    370                 375                 380

Asp Asp Tyr Asn Ala Leu Gln Arg Asp Leu Lys Ile Asp Gly Gly Leu
385                 390                 395                 400

Lys Pro Val Thr Glu Asp Glu Ile Val Lys Val Arg Asn Lys Ala Ala
                405                 410                 415

Arg Ala Ile Gln Gly Leu Phe Lys Glu Leu Asp Leu Pro Glu Ile Thr
            420                 425                 430

Asp Glu Glu Val Glu Ala Ala Thr Tyr Ala His Gly Ser Val Asp Met
        435                 440                 445

Pro Ala Arg Asn Val Val Glu Asp Leu Lys Ala Ala Glu Glu Leu Leu
    450                 455                 460

Ser Ser Gly Ile Thr Gly Val Asp Leu Val Lys Gly Leu Ser Arg Ser
465                 470                 475                 480

Gly Phe Asp Asp Val Ala Glu His Val Leu Gly Met Leu Lys Gln Arg
                485                 490                 495

Val Ser Gly Asp Tyr Leu Gln Thr Ser Ala Ile Leu Asp Lys Gly Phe
            500                 505                 510

Lys Ile Lys Ser Ala Ile Asn Asp Arg Asn Asp Tyr Met Gly Pro Gly
        515                 520                 525

Ser Gly Tyr Arg Ile Ser Glu Glu Arg Trp Glu Glu Ile Lys Asn Ile
    530                 535                 540

Pro Ser Ala Ile Lys Pro Glu Ser Ile Glu
545                 550

<210> SEQ ID NO 46
<211> LENGTH: 187
<212> TYPE: PRT
<213> ORGANISM: Ilyobacter polytropus
<220> FEATURE:
<221> NAME/KEY: MISC_FEATURE
<222> LOCATION: (1)..(187)
<223> OTHER INFORMATION: DhaB2 protein

<400> SEQUENCE: 46

Met Glu Asn Lys Phe Val Pro Ser Val Lys Ile Glu Glu Ile Gly Glu
1               5                   10                  15

Ala Lys Lys Gly Ser Arg Ser Glu Glu Val Val Ile Gly Leu Ala Pro
            20                  25                  30

Ala Phe Lys Lys Phe Gln His Lys Thr Ile Thr Asp Val Pro His Asp
        35                  40                  45

Glu Val Leu Thr Glu Leu Ile Ala Gly Ile Glu Glu Glu Gly Leu Lys
```

```
            50                  55                  60
Ala Arg Ile Val Arg Val Thr Arg Thr Ser Asp Val Ser Phe Met Ala
 65                  70                  75                  80

Leu Asp Ala Ala Lys Leu Ser Gly Ser Gly Ile Gly Ile Gly Ile Gln
                 85                  90                  95

Ser Lys Gly Thr Thr Val Ile His Gln Lys Asp Leu Leu Pro Leu Asn
            100                 105                 110

Asn Leu Glu Leu Phe Pro Gln Ala Pro Leu Leu Thr Pro Glu Thr Phe
        115                 120                 125

Arg Leu Ile Gly Lys Asn Ala Ala Lys Tyr Ala Lys Gly Glu Ser Pro
    130                 135                 140

Asn Pro Val Pro Val Ala Ser Asp Gln Met Ala Arg Pro Lys Tyr Gln
145                 150                 155                 160

Ala Lys Ala Ala Leu Leu His Ile Lys Glu Thr Lys His Val Val Gln
                165                 170                 175

His Gly Lys Pro Val Glu Ile Lys Tyr Glu Phe
            180                 185
```

<210> SEQ ID NO 47
<211> LENGTH: 143
<212> TYPE: PRT
<213> ORGANISM: Ilyobacter polytropus
<220> FEATURE:
<221> NAME/KEY: MISC_FEATURE
<222> LOCATION: (1)..(143)
<223> OTHER INFORMATION: DhaB3 protein

<400> SEQUENCE: 47

```
Met Asn Ile Asp Val Lys Asn Ile Asn Pro Ile Ser Asp Tyr Pro Leu
 1               5                  10                  15

Gly Glu Lys Arg Lys Glu Trp Leu Lys Thr Ser Thr Gly Lys Thr Leu
             20                  25                  30

Asp Glu Ile Thr Leu Glu Asn Val Ile Asn Gly Asp Ile Lys Pro Glu
         35                  40                  45

Asp Ile Arg Ile Ser Pro Glu Thr Leu Lys Leu Gln Gly Glu Ile Ala
     50                  55                  60

Lys Lys Gly Asn Arg Pro Thr Ile Thr Lys Asn Phe Glu Arg Ala Ser
 65                  70                  75                  80

Glu Met Val Ala Ile Pro Asp Asp Lys Ile Leu Ala Thr Tyr Asn Ala
                 85                  90                  95

Leu Arg Pro Tyr Arg Ser Ser Lys Glu Glu Leu Phe Glu Ile Ala Asp
            100                 105                 110

Glu Leu Glu Ser Lys Tyr Ser Ala Val Val Ile Ser Ala Phe Ile Lys
        115                 120                 125

Glu Ala Ala Glu Val Tyr Glu Gln Arg Gly Gln Leu Arg Lys Asp
    130                 135                 140
```

<210> SEQ ID NO 48
<211> LENGTH: 397
<212> TYPE: PRT
<213> ORGANISM: Ralstonia eutropha
<220> FEATURE:
<221> NAME/KEY: MISC_FEATURE
<222> LOCATION: (1)..(397)
<223> OTHER INFORMATION: gabD protein

<400> SEQUENCE: 48

```
Met His Ala Ala Thr Gln Ala Ile Leu Thr Phe Asn His Gly Arg Asp
 1               5                  10                  15
```

-continued

```
Pro Glu Arg Leu Thr Arg Lys Leu Ala Ala Ile Ala Ala Asp Pro Phe
         20                  25                  30

Ala Phe Phe Arg Gly Thr Asn His Leu Tyr Ala Ala Ser Leu Arg Asp
         35                  40                  45

Glu Ala Ala Met Cys Asn Ala Pro Ile Thr Tyr Val Cys Gly Asp Leu
 50                  55                  60

His Leu Glu Asn Phe Gly Ser Phe Lys Gly Asp Asn Gly Leu Val Tyr
 65                  70                  75                  80

Phe Asp Leu Asn Asp Phe Asp Asp Ala Leu Val Ala Pro Leu Thr Val
             85                  90                  95

Asp Val Val Arg Met Leu Ser Ser Val Leu Val Ala Ala Gly Gln Leu
            100                 105                 110

Gly Leu Ser Glu Ala Gly Ala Met Arg Ala Cys Glu Ala Met Leu Ser
            115                 120                 125

Thr Tyr Ala Ala Val Leu Gln Thr Gly Lys Pro Arg Trp Leu Glu Arg
130                 135                 140

Ala Thr Ala Val Gly Met Val Ala Thr Leu Leu Arg Arg Val Lys Gly
145                 150                 155                 160

Arg Lys Arg Gly Ala Leu Leu Ala Glu Leu Thr Thr Leu Arg Lys Gly
                165                 170                 175

Lys Arg Arg Leu Val Cys Asn Gly Arg His Ala Leu Pro Ala Asp Lys
                180                 185                 190

Pro Ala Arg Glu Arg Ala Arg Ala Ile Leu Ala Ala Tyr Ser Lys Gln
            195                 200                 205

Gly His His Gly His Arg Leu Ala Leu Asp Asp Ala Ala Arg Arg Val
        210                 215                 220

Ala Gly Ile Gly Ser Leu Gly Leu Glu Arg Tyr Met Val Leu Ala Arg
225                 230                 235                 240

Asp Glu Leu Ser Gly Met Gln Arg Leu Val Asp Ile Lys Arg Ala Ala
                245                 250                 255

Pro Ser Pro Trp Gln Asp Leu Pro Ser Leu Ser Leu Pro Pro Trp Gly
                260                 265                 270

Ser Asp Ala Arg Arg Val Ala Ala Val Gln Gln Val Met Gln Ala Ala
            275                 280                 285

Ser Pro Ala Leu Leu Ser Ala Val Asp Met Gly Lys Ala Ser Tyr Leu
        290                 295                 300

Val Lys Ser Leu Gln Pro Thr Ala Asp Arg Val Asp Leu Ala His Cys
305                 310                 315                 320

Ser Asn Phe Ala Ala Leu Arg Glu Leu Leu Gly Thr Met Ala His Ala
                325                 330                 335

Ala Ala Trp Ala His Leu Arg Gly Cys Gly His Gln Ala Ala Asp Arg
            340                 345                 350

Ile Glu Gln Leu Gln Ala Phe Ala Gly Gly Thr Arg Trp Arg Thr Gly
        355                 360                 365

Val Leu Arg Leu Ala Arg His Gly Cys Ala Val Ser Val Val Gln Trp
    370                 375                 380

Lys Ala Tyr Ala Asp Asp Tyr Arg Glu Ala Arg Gly Gly
385                 390                 395
```

RECOMBINANT MICROORGANISM WITH ABILITY TO PRODUCE GLYCEROL, 3-HP, OR ACRYLIC ACID AND METHOD OF PRODUCING GLYCEROL, 3-HP, OR ACRYLIC ACID BY USING THE SAME

RELATED APPLICATION

This application claims the benefit of Korean Patent Application No. 10-2014-0034131, filed on Mar. 24, 2014, in the Korean Intellectual Property Office, the entire disclosure of which hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: One 76,853 Byte ASCII (Text) file named "718161_ST25-Revised.TXT" created Dec. 16, 2014.

BACKGROUND

1. Field

The present disclosure relates to recombinant microorganisms that produce glycerol, 3-hydroxypropionic acid (HP), or acrylic acid, and methods of producing glycerol, 3-HP, or acrylic acid using the recombinant microorganisms.

2. Description of the Related Art

Carbon emission reduction and instability caused by the surge in oil prices have been recently considered global issues, and accordingly, efforts have been made to produce fuels or chemicals via carbon-neutral biological processes in place of the existing fuels or chemicals that were produced via chemical processes using oil as a raw material.

Glycerol is a compound that is necessary for cosmetics, liquid soaps, medicines, lubricants, anti-coagulate solutions, and many different industrial applications. Microorganisms that are capable of producing glycerol in various physiological conditions are demanded in a variety of industries. Thus, microorganisms that are capable of producing glycerol in physiological conditions by which glycerol itself is used as a substrate in vivo in a part of a further complicated catabolic or biosynthesis pathway are demanded.

With regard to metabolic pathways of synthesizing glycerol, dihydroxyacetone phosphate (DHAP) produced from glucose is converted into glycerol-3-phosphate (G3P), and G3P is converted into glycerol. Dehydrogenase (G3PDH) may be involved in the conversion of DHAP into G3P, and G3P phosphatase may be involved in the conversion of G3P into glycerol.

There remains a need for alternative microorganisms with the ability to produce glycerol and methods of producing glycerol by using the alternative microorganisms.

SUMMARY

Provided is a recombinant microorganism having an increased ability to produce glycerol 3-HP, and 3-acrylic acid compared to an unmodified microorganism of the same type.

In one embodiment, provided is a recombinant microorganism comprising: a polynucleotide encoding dihydroxyacetone phosphate phosphatase (DHAPP) that catalyzes the conversion of dihydroxyacetone phosphate (DHAP) into dihydroxyacetone (DHA); and a polynucleotide encoding glycerol dehydrogenase (GLDH) that catalyzes the conversion of DHA into glycerol.

In another embodiment, the recombinant microorganism further comprises a polynucleotide encoding glycerol dehydratase (GDH) that catalyzes the conversion of glycerol into 3-hydroxypropionaldehyde (3-HPA); and a polynucleotide encoding an aldehyde dehydrogenase (ALD) that catalyzes the conversion of 3-HPA into 3-hydroxypropionic acid (3-HP).

In an additional embodiment, the recombinant microorganism further comprises: an enzyme that converts 3-HP into 3-HP-CoA; and an enzyme that converts 3-HP-CoA into acryloyl-CoA.

Also provided is a method of efficiently producing glycerol using a recombinant microorganism according to the invention.

According to another aspect of the present invention, provided is a method of efficiently producing 3-HP using a recombinant microorganism according to the invention.

According to another aspect of the present invention, provided is a method of efficiently producing acrylic acid using a recombinant microorganism according to the invention.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
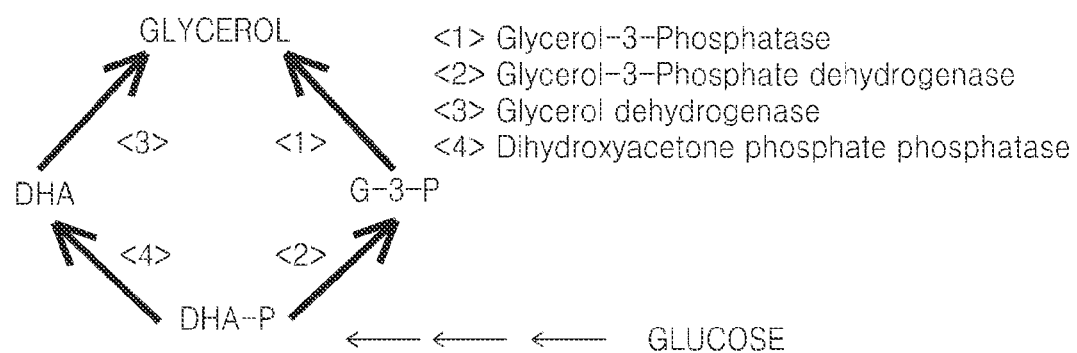
FIG. 1 is a diagram displaying a biosynthesis pathway of producing glycerol from glucose.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

A "sequence identity" of nucleic acid or polypeptide according to an embodiment of the present invention refers to the extent of identity between bases or amino acid residues after aligning the sequences such that they maximally match in certain comparative regions. The sequence identity is a value calculated by optimally aligning two sequences at certain comparative regions, wherein portions of the sequences at the certain comparative regions may be added or deleted, compared to reference sequences. A percentage of the sequence identity may be calculated by, for example, comparing two optimally aligned sequences in the entire comparative region, determining the number of locations in which the same amino acids or nucleic acids appear to obtain the number of matched locations, dividing the number of matched locations by the total number of locations in the comparative regions (that is, the size of the range), and multiplying by 100 to calculate the percentage of the sequence identity. The percentage of the sequence identity may be calculated by using a known sequence comparison program, and examples of the program include BLASTN (NCBI), CLC Main Workbench (CLC bio), and MegAlign™ (DNASTAR Inc).

Various levels of sequence identity may be used to identify various types of polypeptides or polynucleotides having the same or similar functions. For example, a sequence identity of about 50% or more, about 55% or more, about 60% or more, about 65% or more, about 70% or more, about 75% or more, about 80% or more, about 85% or more, about 90% or more, about 95% or more, about 96% or more, about 97% or more, about 98% or more, about 99% or more, or 100% may be used.

According to an aspect of the present invention, provided is a recombinant microorganism including a polynucleotide encoding dihydroxyacetone phosphate phosphatase (DHAPP) that catalyzes the conversion of dihydroxyacetone phosphate (DHAP) into dihydroxyacetone (DHA); and a polynucleotide encoding glycerol dehydrogenase (GLDH) that catalyzes the conversion of DHA into glycerol. The recombinant microorganism may produce an increased amount of glycerol compared to an unmodified organism of the same type.

As used herein, the term "DHAPP" refers to any enzyme that catalyzes the conversion of DHAP into DHA. The DHAPP may belong to the haloacid dehydrogease superfamily (HAD family). The HAD family may have phosphatase activity of P-type ATPase. The HAD family may not exhibit any phosphatase activity, or have almost no phosphatase activity, with respect to nucleoside monophosphates (i.e., AMP, CMP, GMP, or UMP), for example, when the nucleotide monophosphates are at a concentration of 5 to 10 mM in a solution and or cell culture medium with a member of the HAD family. The DHAPP may be HAD superfamily phosphatase A (HdpA) derived from *C. glutamicum*. The HdpA may have an amino acid sequence of SEQ ID NO: 1. The polynucleotide encoding the HdpA may have a nucleotide sequence encoding an amino acid sequence of SEQ ID NO: 1, for example, a nucleotide sequence of SEQ ID NO: 2. The DHAPP may include an amino acid sequence having a sequence identity of about 65% or more, for example, about 70% or more, about 80% or more, about 85% or more, about 90% or more, about 91% or more, about 92% or more, about 93% or more, about 94% or more, about 95% or more, about 96% or more, about 97% or more, about 98% or more, about 99% or more, or about 100% to SEQ ID NO: 1. The DHAPP may be phospholipid-translocating ATPase categorized as EC 3.6.3.1, 3-deoxy-D-manno-octulosonate (KDO) 8-phosphate phosphatase categorized as EC 3.1.3.45, mannosyl-3-phosphoglycerate phosphatase categorized as EC 3.1.3.70, or phosphoglycolate phosphatase categorized as EC 3.1.3.18. The DHAPP may be a polypeptide belonging to the HAD superfamily that has NCBI IDs listed in Table 1. The polynucleotide encoding DHAPP may be heterologous to the recombinant microorganism.

TABLE 1

| NCBI ID | Microorganism |
|---|---|
| gi\|25028706 | *Corynebacterium efficiens* YS.314 |
| gi\|334564111 | *Corynebacterium bovis* DSM20582 |

TABLE 1-continued

| NCBI ID | Microorganism |
|---|---|
| gi\|38234264 | *Corynebacterium diphtheriae* NCTC13129 |
| gi\|337291210 | *Corynebacterium ulcerans* BR.AD22 |
| gi\|300858925 | *Corynebacterium pseudotuberculosis* FRC41 |
| gi\|255324876 | *Corynebacterium tuberculostearicum* SK141 |
| gi\|227833577 | *Corynebacterium aurimucosum* ATCC700975 |
| gi\|227503202 | *Corynebacterium accolens* ATCC49725 |
| gi\|296119783 | *Corynebacterium ammoniagenes* DSM20306 |
| gi\|227504606 | *Corynebacterium striatum* ATCC6940 |
| gi\|358445640 | *Corynebacterium casei* UCMA3821 |
| gi\|237785884 | *Corynebacterium kroppenstedtii* DSM44385 |
| gi\|54027323 | *Nocardia farcinica* IFM10152 |
| gi\|300790316 | *Amycolatopsis mediterranei* U32 |
| gi\|375102711 | *Saccharomonospora cyanea* NA.134 |
| gi\|72162161 | *Thermobifida fusca* YX |
| gi\|357413254 | *Streptomyces favogriseus* ATCC33331 |
| gi\|297561702 | *Nocardiopsis dassonvillei* subsp. *dassonvillei* DSM43111 |
| gi\|262200628 | *Gordonia bronchialis* DSM43247 |
| gi\|134097184 | *Saccharopolyspora erythraea* NRRL2338 |
| gi\|358457856 | *Frankia* sp. CN3 |
| gi\|312141254 | *Rhodococcus equi* 103S |
| gi\|324997972 | *Pseudonocardia* sp. P1 |
| gi\|377575652 | *Mobilicoccus pelagius* NBRC104925 |
| gi\|357389721 | *Kitasatospora setae* KM.6054 |
| gi\|325961988 | *Arthrobacter phenanthrenivorans* Sphe3 |
| gi\|326331131 | *Nocardioidaceae bacterium* Broad.1 |
| gi\|258654845 | *Nakamurella multipartita* DSM44233 |
| gi\|302868690 | *Micromonospora aurantiaca* ATCC27029 |
| gi\|330469082 | *Verrucosispora maris* AB.18.032 |
| gi\|296138280 | *Tsukamurella paurometabola* DSM20162 |
| gi\|152968106 | *Kineococcus radiotolerans* SRS30216 |
| gi\|118470582 | *Mycobacterium smegmatis* MC2.155 |
| gi\|159038790 | *Salinispora arenicola* CMS.205 |
| gi\|148271663 | *Clavibacter michiganensis* subsp. *michiganensis* NCPPB382 |
| gi\|333922006 | *Amycolicicoccus subflavus* DQS3.9A1 |
| gi\|334335848 | *Isoptericola variabilis* 225 |
| gi\|379737345 | *Blastococcus saxobsidens* DD2 |
| gi\|359834376 | *Actinoplanes* sp. SE50/110 |
| gi\|296130804 | *Cellulomonas flavigena* DSM20109 |
| gi\|256374626 | *Actinosynnema mirum* DSM43827 |
| gi\|271964711 | *Streptosporangium roseum* DSM43021 |
| gi\|309811927 | *Dermacoccus* sp. Ellin185 |
| gi\|284992561 | *Geodermatophilus obscurus* DSM43160 |

As used herein, the term "GLDH" may be any material as long as it catalyzes the conversion of DHA into glycerol. The GLDH may be a polypeptide that catalyzes the conversion of DHA into glycerol. The GLDH may be an enzyme categorized as EC 1.1.1.6. The GLDH may also be DHA reductase. The GLDH may be dependent on NAD categorized as EC 1.1.1.6, NADP categorized as EC 1.1.1.72, or other cofactors categorized as, for example, EC 1.1.99.22. An example of the NAD-dependent GLDH is gldA (GenBank U000006) having an amino acid sequence of SEQ ID NO: 3. In addition, the polynucleotide encoding the GLDH may have a nucleotide sequence encoding an amino acid sequence of SEQ ID NO: 3, for example, a nucleotide sequence of SEQ ID NO: 4. The GLDH may include an amino acid sequence having a sequence identity of about 65% or more, for example, about 70% or more, about 80% or more, about 85% or more, about 90% or more, about 91% or more, about 92% or more, about 93% or more, about 94% or more, about 95% or more, about 96% or more, about 97% or more, about 98% or more, about 99% or more, or about 100% to SEQ ID NO: 3. The polynucleotide encoding GLDH may be heterologous to the recombinant microorganism.

The DHAPP-coding polynucleotide and/or the GLDH-coding polynucleotide may be expressed at higher levels in the recombinant microorganism than those in a microorganism that is not genetically manipulated. The expression level may refer to the expression of mRNA or protein encoded by the mRNA. The expression at the protein level may be based on amount of protein expressed or the activity of the expressed protein. The expression level may be increased by about 5% or more, about 10% or more, about 15% or more, about 20% or more, about 30% or more, about 50% or more, about 60% or more, about 70% or more, about 100% or more, about 200% or more, or about 300% or more than that in a microorganism that is not genetically manipulated. The term "microorganism that is not genetically manipulated" as used herein may be a parent cell or microorganism that is not genetically manipulated or genetically engineered, for example, a parent microorganism that does not contain the DHAPP-coding polynucleotide and/or the GLDH-coding polynucleotide, or that contains fewer copies of the DHAPP-coding polynucleotide and/or GLDH-coding polynucleotide.

The recombinant microorganism may have the ability to produce glycerol. The recombinant microorganism may produce glycerol at higher levels than a parent microorganism that is not genetically manipulated. The production of glycerol may include production in a cell, secretion of glycerol from the cell (e.g., in a cell culture medium) after being produced in a cell, or a combination thereof. Glycerol produced in a cell may be converted from metabolites such as 3-HP or acrylic acid. The production of glycerol may be increased by about 5% or more, about 10% or more, about 15% or more, about 20% or more, about 30% or more, about 50% or more, about 60% or more, about 70% or more, about 100% or more, about 200% or more, or about 300% or more than that in a microorganism that is not genetically manipulated.

The increase in the expression level of polynucleotides, proteins, or enzymes used in embodiments of the present invention may occur by introducing a polynucleotide encoding a polypeptide (i.e., enzyme) into a cell, increasing a copy number of the polynucleotide in the cell, or mutating a regulatory region of the polynucleotide. A polynucleotide that is introduced from the outside or present in an increased copy number may be an endogenous gene or an exogenous gene. The endogenous gene refers to a gene that exists in a genetic material included in a microorganism. The exogenous gene refers to a gene that is introduced into a host cell, such as a gene that is integrated into a host cell genome, wherein the introduced gene may be homologous or heterologous with respect to the host cell genome.

The expression "increased copy number" as used herein may include a copy number increase by an introduction or amplification of the gene and a genetic manipulation of a cell that does not have a gene so as to have the gene in the cell. The introduction of the gene may occur by using a vehicle such as a vector. The vector may be delivered to the microorganism using a variety of techniques e.g., incubation in a solution containing divalent cations followed by heat shock and electroporation, or other suitable transformation techniques known in the art. The introduction may be a transient introduction, in which the gene is not integrated into the genome, or an integration into the genome. The introduction may, for example, occur by introducing a vector inserted with a polynucleotide encoding a desired polypeptide into the genome of the cell and then replicating the vector in the cell or integrating the polynucleotide into the genome.

The term "gene" as used herein refers to a nucleic acid fragment expressing a specific protein, and may include a regulatory sequence such as 5'-non coding sequence and 3'-non coding sequence in addition to a coding region.

The term "heterologous" as used herein refers to foreign matter that is not native to the cell.

The term "secretion" as used herein refers to a movement of a material from cell interior to a periplasmic space or an extracellular environment.

The recombinant microorganism may be a prokaryote. The recombinant microorganism may be a bacterium, and examples thereof include *Escherichia* such as *Escherichia coli*, *Clostritidia* such as *Clostritidium ljungdahlii*, *Clostritidium autoethanogenum* or *Clostritidium kluyveri*, *Corynebacteria* such as *Corynebacterium glutamicum*, *Cupriavidus* such as *Cupriavidus necator* or *Cupriavidus metallidurans*, *Pseudomonas* such as *Pseudomonas fluorescens*, *Pseudomonas putida* or *Pseudomonas oleavorans*, *Delftia* such as *Delftia acidovorans*, *Bacillus* such as *Bacillus subtilis*, *Lactobacillus* such as *Lactobacillus delbrueckii*, or *Lactococcus* genus including *Lactococcus lactis*. *Corynebacteria* genus may include *C. callunae*, *C. efficiens*, *C. ulcerans*, *C. halotolerans*, *C. pseudotuberculosis*, *C. durum*, or *C. striatum*. These bacteria may act as a host cell for the recombinant microorganism.

The recombinant microorganism may be a eukaryote, and the eukaryote may be fungi such as yeasts. The eukaryote may be *Aspergillus* genus including *A. niger*, *Saccharomyces* genus including *S. cerevisiae*, *Pichia* genus including *P. pastoris*, *Yarrowia* genus including *Y. lipolytica*, *Issatchenkia* genus including *I. orientalis*, *Debaryomyces* genus including *D. hansenii*, *Arxula* genus including *A. adenoinivorans*, *Kluyveromyces* genus including *K. lactis*, or *Hypocrea* genus including *H. americana*. These microorganisms may act as a host cell for the recombinant microorganism. The *Saccharomyces* genus may not include *S. pombe*.

The recombinant microorganism is genetically manipulated, as compared to a parent microorganism. Such manipulation may include introducing a polynucleotide encoding a polypeptide into a cell (e.g., a non-native polynucleotide), increasing a copy number of the polynucleotide in the cell (e.g., a native polynucleotide), or mutating a regulatory region of a polynucleotide (e.g., of a native polynucleotide). A polynucleotide that is introduced from the outside or present in an increased copy number may be an endogenous gene or an exogenous gene. The endogenous gene refers to a gene that exists in a genetic material natively included in a microorganism. The exogenous gene refers to a gene that is introduced into a host cell, such as a gene that is integrated into a host cell genome, wherein the introduced gene may be homologous or heterologous with respect to the host cell genome. The recombinant microorganism may be manipulated, as compared to the polypeptide or the gene used in the present specification.

The recombinant microorganism may further include a polynucleotide encoding glycerol dehydratase (GDH) that catalyzes the conversion of glycerol into 3-hydroxypropionaldehyde (3-HPA); and a polynucleotide encoding aldehyde dehydrogenase (ALD) that catalyzes the conversion of 3-HPA into 3-hydroxypropionic acid (3-HP). The polynucleotide encoding GDH may be heterologous to the microorganism. The recombinant microorganism may produce an increased amount of 3-HP compared to an unmodified microorganism of the same type (e.g., a parent microorganism).

The term "GDH" as used herein may include any enzyme as long as it is catalyzes the conversion of glycerol into 3-HPA. The GDH may be categorized as EC 4.2.1.30 or may be a diol dehydratase categorized as EC 4.2.1.28. The GDH and a nucleotide encoding GDH may be derived from *Ilyobacter polytropus*, *Klebsiella pneumoniae*, *Citrobacter freundii*, *Clostritidium pasteurianum*, *Salmonella typhimurium*, or *Klebsiella oxytoca*. In each case of these genra, the GDH may be composed of three subunits: a large or "α" subunit, a medium or "β" subunit, and a small or "γ" subunit. A gene encoding the large or "α" subunit of the GDH may include dhaB1, gldA, and dhaB. A gene encoding the medium or "β" subunit of the GDH may include dhaB2, gldB, and dhaC. A gene encoding the small or "γ" subunit of the GDH may include dhaB3, gldC, and dhaE. A gene encoding a large or "α" subunit of the diol dehydratase may include pduC and pddA. A gene encoding a medium or "β" subunit of the diol dehydratase may include pduD and pddB. A gene encoding a small or "γ" subunit of the diol dehydratase may include pduE and pddC. Tables 2 and 3 shows a comparison of gene names regarding GDH and functions related to the GDH and GenBank references. The GDH may include dhaB1, dhaB2, and dhaB derived from *Ilyobacter polytropus*. DhaB1, DhaB2, and DhaB3 derived from *Ilyobacter polytropus* may each include an amino acid sequence of SEQ ID NO: 45, 46, and 47. The dhaB1, dhaB2, and dhaB3 genes may each encode an amino acid sequence of SEQ ID NO: 45, 46, and 47. The dhaB1, dhaB2, and dhaB3 genes derived from *Ilyobacter polytropus* may each have a sequence of SEQ ID NO: 5, 6, and 7.

TABLE 2

| Individual (GenBank reference number) | Gene function | | | | | | | |
|---|---|---|---|---|---|---|---|---|
| | Regulation | | Unknown | | Reactivation | | Unknown | |
| | Gene | Base pair | Gene | Base pair | Gene | Base pair | Gene | Base pair |
| K. pneumoniae (U30903) | | | orf2c | 7116-7646 | orf2b | 6762-7115 | orf2a | 5125-5556 |
| K. pneumoniae (U60992) | | | | | GdrB | | | |
| C. freundii (U09771) | dhaR | 3746-5671 | orfW | 5649-6179 | orfX | 6180-6533 | orfY | 7736-8164 |
| C. pasteurianum (AF051373) | | | | | | | | |
| C. pasteurianum (AF026270) | | | orfW | 210-731 | orfX | 1-196 | orfY | 746-1177 |
| S. typhimurium (AF026270) | | | | | pduH | 8274-8645 | | |
| K. oxytoca (AF017781) | | | | | DdrB | 2063-2440 | | |
| K. oxytoca (AF051373) | | | | | | | | |

TABLE 3

| Individual (GenBank reference number) | Gene function | | | | | | | |
|---|---|---|---|---|---|---|---|---|
| | Dehydratase, α | | Dehydratase, α | | Dehydratase, α | | Reactivation | |
| | Gene | Base pair | Gene | Base pair | Gene | Base pair | Gene | Base pair |
| K. pneumoniae (U30903) | dhaB1 | 3047-4714 | dhaB2 | 2450-2890 | dhaB3 | 2022-2447 | orf2a | 186-2009 |
| K. pneumoniae (U60992) | gldA | 121-1788 | gldB | 1801-2382 | gldB | 2388-2813 | gdrA | |
| C. freundii (U09771) | dhaB | 8556-10223 | dhaC | 10235-10819 | dhaC | 10822-11250 | orfY | 11261-13072 |
| C. pasteurianum (AF051373) | dhaB | 84-1748 | dhaC | 1779-2318 | dhaC | 2333-2773 | | 2790-4598 |
| C. pasteurianum (AF026270) | | | | | | | orfY | |
| S. typhimurium (AF026270) | pduC | 3557-5221 | pduD | 5232-5906 | pduD | 5921-6442 | | 6452-8284 |
| K. oxytoca (AF017781) | | | | | | | | 241-2073 |
| K. oxytoca (AF051373) | pddA | 121-1785 | pddB | 1796-2470 | pddB | 2485-3006 | | |

The GDH may include an amino acid sequence derived from *Ilyobacter polytropus*, the amino acid sequence having a sequence identity of about 65% or more, for example, about 70% or more, about 80% or more, about 85% or more, about 90% or more, about 91% or more, about 92% or more, about 93% or more, about 94% or more, about 95% or more, about 96% or more, about 97% or more, about 98% or more, about 99% or more, or about 100% to each sequence of dhaB1, dhaB2, and dhaB3.

The term "ALD" as used herein may include any protein as long as it is capable of catalyzing the conversion of 3-HPA into 3-HP. The ALD may use redox cofactors, such as NAD, NADP, FAD, or PQQ. The ALD may be categorized as EC 1.2.1.3 (NAD-dependent ALD), EC 1.2.1.4 (NADP-dependent ALD), EC 1.2.99.3 (PQQ-dependent ALD), or EC 1.2.99.7 (FAD-dependent ALD). An example of the NADP-dependent ALD includes AldB encoded by aldB gene of *E. coli*. An example of the NAD-dependent ALD includes AldA encoded by aldA gene of *E. coli* or AldH encoded by aldH gene of *E. coli*. The ALD may be succinate semialdehyde dehydrogenase (SSADH). The SSADH may be categorized as EC 1.2.1.24 or EC 1.2.1.16. The SSADH may be dependent on NAD+, NADP+, or both NAD+ and NADP+. The SSADH may be CoA-independent enzyme. The SSADH may be, for example, derived from *Corynebacterium* sp., *Rhodococcus* sp., *Gordonia* sp., *Mycobacterium* sp., *Enterobacter* sp., or *Aserica* sp. The SSADH may be gabD1, gabD2, or gabD3 derived from *E. coli*. A gene encoding the SSADH may be, for example, a polynucleotide encoding an amino acid sequence of SEQ ID NO: 8, 9, and 10. The SSADH may be gabD (a nucleotide sequence of SEQ ID NO: 36 and an amino acid sequence of SEQ ID NO: 48) derived from *Cupriavidus necator*. A gene encoding the SSADH may be, for example, a polynucleotide encoding an amino acid sequence of SEQ ID NO: 8, 9, 10, and 36. A gene encoding the SSADH may include, for example, a nucleotide sequence of SEQ ID NO: 11, 12, 13, and 36. The SSADH may include an amino acid sequence having a sequence identity of about 65% or more, for example, about 70% or more, about 80% or more, about 85% or more, about 90% or more, about 91% or more, about 92% or more, about 93% or more, about 94% or more, about 95% or more, about 96% or more, about 97% or more, about 98% or more, about 99% or more, or about 100% to amino acid sequences of SEQ ID NO: 8, 9, 10, and 48.

The recombinant microorganism may further include a polynucleotide encoding glycerol dehydratase reactivase (GDR). Glycerol and diol dehydratases may be subjected to metabolism-based suicide inactivation by glycerol and some other substrates (see e.g., Daniel et al., FEMS Microbiol. Rev. 22, 553(1999)). The term "glycerol dehydratase reactivase (GDR)" as used herein refers to proteins responsible for reactivating the dehydratase activity. The term "dehydratase reactivating activity" as used herein refers to the phenomenon of converting a dehydratase that is unable to catalyze a substrate into a dehydratase capable of catalyzing a substrate, or to the phenomenon of inhibiting the degradation of a dehydratase, or the phenomenon of extending the half-life of the dehydratase enzyme in vivo. The GDR may be at least one of dhaB, gdrA, pduG, and ddrA. In addition, the GDR may be at least one of orfX, orf2b, gdrB, pduH, and ddrB.

The GDR, as gdrA and gdrB derived from *K. pneumonia* (U60992), may each have amino acid sequences of SEQ ID NO: 18 and 19. Alternatively, the GDR, as gdrA and gdrB derived from *I. polytropus*, may each have amino acid sequences of SEQ ID NO: 14 and 15. The GDR may have an amino acid sequence having a sequence identity of about 65% or more, for example, about 70% or more, about 80% or more, about 85% or more, about 90% or more, about 91% or more, about 92% or more, about 93% or more, about 94% or more, about 95% or more, about 96% or more, about 97% or more, about 98% or more, about 99% or more, or about 100% to each amino acid sequence of SEQ ID NO: 14, 15, 18, and 19. Genes encoding GdrA and GdrB may have sequences coding each amino acid sequence of SEQ ID NO: 14, 15, 18, and 19, and for example, may have each nucleotide sequence of SEQ ID NO: 16, 17, 20, and 21.

In the recombinant microorganism, at least one polynucleotide selected from the group consisting of a polynucleotide encoding the GDH, a polynucleotide encoding the ALD, and a polynucleotide encoding the GDR may be expressed at higher levels than in a microorganism that is not genetically manipulated (e.g., parent microorganism). The expression level may be an expression at an mRNA or protein level. The expression at the protein level is based on amounts or activities of the expressed proteins. The expression level may be increased by about 5% or more, about 10% or more, about 15% or more, about 20% or more, about 30% or more, about 50% or more, about 60% or more, about 70% or more, about 100% or more, about 200% or more, or about 300% or more than that in a microorganism that is not genetically manipulated, for example, a parent cell.

In some embodiments, the recombinant microorganism may produce 3-HP. In this regard, the increase in the expression level may refer to production of 3-HP at higher levels than that in a microorganism that is not genetically manipulated (e.g., parent microorganism). The production of 3-HP may include production in a cell, secretion to the outside after being produced in a cell, or a combination thereof. 3-HP produced in a cell may be converted from other metabolites such as acrylic acid. The production of 3-HP may be increased by about 5% or more, about 10% or more, about 15% or more, about 20% or more, about 30% or more, about 50% or more, about 60% or more, about 70% or more, about 100% or more, about 200% or more, or about 300% or more than that in a microorganism that is not genetically manipulated, for example, a parent cell.

The increase in the expression level may be due to any mode of genetic manipulation as described, above (e.g., introducing a new polynucleotide, increasing the copy number of an existing polynucleotide, or mutating a regulatory region). The recombinant microorganism may further include a polynucleotide encoding an enzyme that catalyzes the conversion 3-HP into 3-HP-CoA; and another polynucleotide encoding an enzyme that catalyzes the conversion of 3-HP-CoA into acryloyl-CoA and/or acrylate. The recombinant microorganism may further include a polynucleotide encoding an enzyme (e.g., acryloyl-CoA hydrolase) that catalyzes the conversion acryloyl-CoA into acrylate.

The enzyme that catalyzes the conversion of 3-HP into 3-HP-CoA may be a polypeptide having CoA transferase activity, a polypeptide having 3-HP CoA hydrolase activity, or a polypeptide having 3-hydroxyisobutyryl-CoA hydrolase activity. The polypeptide having CoA transferase activity may be categorized as EC 2.8.3.1. The polypeptide having CoA transferase activity or a polynucleotide encoding the same may be derived from *Megasphaera elsdenii, Clostritidium propionicum, Clostritidium kluyveri,* and *Escherichia coli*. The polypeptide having CoA transferase activity may be Pct (SEQ ID NO: 22) derived from *M. elsdenii* ATCC17753 CoA transferase, and the gene encoding the same may be pct (SEQ ID NO: 23). The polypeptide having 3-HP CoA hydrolase activity may be categorized as EC 3.1.2.-. The enzyme categorized as EC 3.1.2.- may be a gene product, such as YciA, tesB, or Acot13. The polypeptide having 3-hydroxypropionly-CoA hydrolase activity and a polynucleotide encoding the same may be a yciA gene product (SEQ ID NO: 24) of *E. coli* K-12 W3110 and the gene of the same (SEQ ID NO: 25). The polypeptide having 3-hydroxyisobutyryl-CoA hydrolase activity may be categorized as EC 3.1.2.4.

The enzyme that catalyzes the conversion of 3-HP-CoA into acryloyl-CoA or acrylate may be a polypeptide having activity of 3-hydroxypropionyl-CoA dehydratase. The conversion of acrylate of acryloyl-CoA into acrylic acid may be achieved by intracellular CoA ligase. The bacterial cells may be capable of expressing CoA ligase, and may have genes encoding CoA ligase. The polypeptide having activity of 3-hydroxypropionyl-CoA dehydratase may be categorized as EC 4.2.1.-. The polypeptide having activity of 3-hydroxypropionyl-CoA dehydratase or a polynucleotide encoding the same may be derived from *Chloroflexus aurantiacus, Candida rugosa, Rhodospirillum rubrum,* or *Rhodobacter capsulates*. The polypeptide having activity of 3-hydroxypropionyl-CoA dehydratase or the polynucleotide encoding the same, i.e., HPD and hpd derived from *C. aurantiacus*, may each have an amino acid sequence of SEQ ID NO: 26 and a nucleotide sequence of SEQ ID NO: 27.

In the recombinant microorganism, at least one polynucleotide selected from the group consisting of a polynucleotide encoding an enzyme that converts 3-HP into 3-HP-CoA and a polynucleotide encoding an enzyme that converts 3-HP-CoA into acryloyl-CoA and/or acrylate may be expressed at higher levels than in a microorganism that is not genetically manipulated. The expression level may be an expression at an mRNA or protein level. The expression at the protein level is based on amounts or activities of the expressed proteins. The expression level may be increased by about 5% or more, about 10% or more, about 15% or more, about 20% or more, about 30% or more, about 50% or more, about 60% or more, about 70% or more, about 100% or more, about 200% or more, or about 300% or more than that in a microorganism that is not genetically manipulated.

In additional embodiments, the recombinant microorganism may have the ability to produce acrylic acid and/or acrylate. In this regard, the increase in the expression level may refer to production of acrylic acid and/or acrylate at higher levels than that in a microorganism that is not genetically manipulated. The production of acrylic acid and/or acrylate may include production in a cell, secretion to the outside after being produced in a cell, or a combination thereof. 3-HP produced in a cell may be converted from other metabolites such as acrylic acid. The production of acrylic acid and/or acrylate may be increased by about 5% or more, about 10% or more, about 15% or more, about 20% or more, about 30% or more, about 50% or more, about 60% or more, about 70% or more, about 100% or more, about 200% or more, or about 300% or more than that in a microorganism that is not genetically manipulated.

The increase in the expression level may be due to any mode of genetic manipulation as described, above (e.g., introducing a new polynucleotide, increasing the copy number of an existing polynucleotide, or mutating a regulatory region). Another aspect of the present invention provides a method of producing glycerol comprising culturing the recombinant microorganism in a cell culture medium, whereby the microorganism produces glycerol; and recovering glycerol from the culture.

Another aspect of the present invention provides a method of producing 3-HP comprising culturing the recombinant microorganism; and recovering 3-HP from the culture.

Another aspect of the present invention provides a method of producing acrylic acid comprising culturing the recombinant microorganism in a cell culture medium, whereby the microorganism produces acrylic acid; and recovering acrylic acid from the culture.

Another aspect of the present invention provides a method of producing 3-hydroxypropionic acid (3-HP), the method comprising:

culturing the recombinant microorganism of claim 7 in a cell culture medium, whereby the microorganism produces 3-HP; and recovering 3-HP from the culture.

The culturing may be performed in a suitable medium under suitable culturing conditions known in the art. For example, the medium may be aqueous solution containing glucose 40 g/l, $MgSO_4 \cdot 7H_2O$ 1.4 g/l, $K_2HP_4$ 17.4 g/l, $KH_2PO_4$ 3.0 g/l, $(NH_4)_2HPO_4$ 4.0 g/l, citric acid 1.7 g/l, $ZnCl_2$ 0.014 g/l, $FeCl_2 \cdot 4H_2O$ 0.041 g/l, $MnCl_2$ 0.015 g/l, $CuCl_2$ 0.0015 g/l, $H_3BO_3$ 0.003 g/l, and $Na_2MoO_4$ 0.0025 g/l. One of ordinary skill in the art may suitably change a culture medium and culturing conditions according to the microorganism selected. Culturing methods may include batch culturing, continuous culturing, fed-batch culturing, or a combination thereof.

The culture medium may include various carbon sources, nitrogen sources, and trace elements.

The carbon source may include assimilable sugars, which may be hexose or pentose sugars. The carbon source may be, for example, carbohydrate such as glucose, sucrose, lactose, fructose, maltose, starch, or cellulose; fat such as soybean oil, sunflower oil, castor oil, or coconut oil; fatty acid such as palmitic acid, stearic acid, linoleic acid; alcohol such as glycerol or ethanol; organic acid such as acetic acid, or a combination thereof. The culturing may be performed by having glucose as the carbon source. The nitrogen source may be an organic nitrogen source such as peptone, yeast extract, beef stock, malt extract, corn steep liquor (CSL), or soybean flour, or an inorganic nitrogen source such as urea, ammonium sulfate, ammonium chloride, ammonium phosphate, ammonium carbonate, and ammonium nitrate, or a combination thereof. The culture medium is a supply source of phosphorus and may include, for example, potassium dihydrogen phosphate, dipotassium phosphate, and corresponding sodium-containing salt thereof, and a metal salt such as magnesium sulfate or iron sulfate. Also, amino acid, vitamin, a suitable precursor, or the like may be included in the culture medium. The culture medium or an individual component may be added to a culture medium solution in a batch, fed-batch, or continuous manner.

Also, the pH of the culture medium solution may not be adjusted or may be adjusted by adding a compound such as ammonium hydroxide, potassium hydroxide, ammonia, phosphoric acid, and sulfuric acid to the culture medium solution by using a suitable method during the culturing process. Also, an antifoaming agent such as fatty acid polyglycol ester may be used during the culturing process to inhibit the generation of bubbles.

The culturing process may be performed under anaerobic or a microaerobic condition. As used herein, the term "anaerobic conditions" refers to an environment devoid of oxygen. As used herein, the term "microaerobic conditions" when used in reference to a culture or growth condition is intended to mean that the dissolved oxygen concentration in the medium remains larger than 0% and less than 10% of saturation for dissolved oxygen in liquid media. Microaerobic conditions also include growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases. The oxygen conditions may include a dissolved oxygen (DO) concentration of 0% to 10%, for example, 0%, 0 to 8%, 0 to 6%, 0 to 4%, 0 to 2%, 1 to 10%, 1 to 8%, 1 to 6%, 1 to 4%, or 1 to 2%, 2 to 10%, 2 to 8%, 2 to 6%, 2 to 4%, 3 to 10%, 3 to 8%, 3 to 6%, 4 to 10%, 4 to 8%, or 4 to 6%.

Glycerol, 3-HP, or acrylic acid produced by the recombinant microorganism may be secreted from the cell, and then recovered from the culture medium. Additionally, glycerol, 3-HP, or acrylic acid may be separated from the culture medium. The separation of glycerol, 3-HP, or acrylic acid from the culture medium may be performed by using separation and purification methods known in the art. The recovering may be performed by centrifugation, chromatography, extraction, filtration, sedimentation, or a combination thereof.

The chemical conversion of glycerol, 3-HP, or acrylic acid produced by the methods above may achieve synthesis of substrates that are structurally related thereto.

Hereinafter, the present invention is described in greater detail with reference to embodiments. However, the embodiments are for illustrative purposes only and do not limit the scope of the present invention.

EXAMPLE 1

Manufacture of Microorganisms Introduced by DHAPP and GLDH Genes and Evaluation of Ability to Produce Glycerol in the Microorganisms (1) Manufacture of a Vector to be Introduced into hdpA and gldA Genes.

Genes (e.g., hdpA of SEQ ID NO: 2) encoding DHAPP derived from *Corynebacterium glutamicum* ATCC 13032 were obtained by PCR amplification using a primer set of hdpA_F (SEQ ID NO: 28) and hdpA_R (SEQ ID NO: 29). The PCR amplification was performed in 30 cycles by repeating the processes of denaturing at a temperature of 95° C. for 30 seconds, annealing at a temperature of 50° C. for 30 seconds, and elongation at a temperature of 72° C. for 1 minute. The amplification products obtained therefrom were processed with restriction enzymes, i.e., NcoI and BamHI, and then cloned in a pACYCDuet™-1 vector (Novagen).

Figure 2:
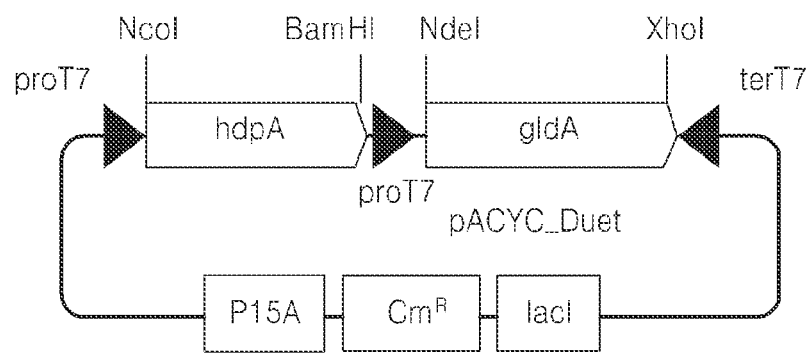
FIG. 2 is a cleavage map of a pACYCDuet_hdpA_gldA vector.

In addition, genes (gldA of SEQ ID NO: 4) encoding GLDH derived from *E. coli* (e.g., *E. coli* K strains) used were obtained by PCR amplification using a primer set of gldA_F (SEQ ID NO: 30) and gldA_R (SEQ ID NO: 31). The PCR amplification was performed in 30 cycles by repeating the processes of denaturing at a temperature of 95° C. for 30 seconds, annealing at a temperature of 50° C. for 30 seconds, and elongation at a temperature of 72° C. for 1 minute. The amplification products obtained therefrom were processed with restriction enzymes, i.e., NdeI and XhoI, and then cloned to the vector above, thereby obtaining a pACYC/hdpA_gldA vector. FIG. 2 is a cleavage map of the pACYCDuet_hdpA_gldA vector.

(2) Evaluation of Glycerol Productivity

The pACYC/hdpA_gldA vector manufactured in step (1) was transformed into *E. coli* K (DE3) strains. The *E. coli* to which the vector was introduced was cultured in an M9 minimal medium (0.4 g/L of $MgSO_4$ $H_2O$, 17.4 g/L of $K_2HPO_4$, 3 g/L of $KH_2PO_4$, 4 g/L of $(NH_4)_2HPO_4$, 1.7 g/L of citric acid, 0.014 g/L of $ZnCl_2$, 0.041 g/L of $FeCl_2$ $H_2O$, 0.015 g/L of $MnCl_2$, 0.0015 g/L of $CuCl_2$, 0.003 g/L of $H_3BO_3$, 0.0025 g/L of $Na_2MoO_4$, 200 mg/L of nitriloacetic acid, 30 μg/L of sodium selenite, and 40 g/L of glycerol) at a temperature of 30° C. until $OB_{600}$ achieved 0.6. of 0.02 mM of IPTG was added thereto, and the medium was cultured again at a temperature of 30° C. for 24 hours. Then, the concentration of glycerol produced in the culture medium was measured. The culturing may be performed by shaking the medium in a 250 mL flask, and then the concentration of acrylic acid was calculated using HPLC.

After culturing the culture medium for 24 hours, portions of the culture medium were extracted for measuring optical density and pH, thereby identifying production of 3-HP by using HPLC (Waters). Once every 24 hours, the pH of the culture medium was corrected to pH 7.0 by using 4N NaOH. In HPLC analysis, an Aminex HPX-87H (300 mm×7.8 mm) column was used, and 0.5 mM of an aqueous solution of sulfuric acid containing 9% acetonitrile was used in a mobile phase. Here, HPLC had a flow rate of 0.4 ml/min and a temperature of 35° C. in the column. A detector device used a dual mode of RI and UV/VIS (210 nm). Glycerol was detected in 16.2 minutes out of 35 minutes in total.

Table 4 below shows produced amounts of glycerol according to consumed amounts of glucose of the *E. coli*. The recombinant strain consumed 20.15 g/L of glucose in 24 hours while it produced 0.85 g/L of glycerol.

TABLE 4

| | Produced amount of glycerol (g/L) | Consumed amount of glucose (g/L) | OD |
|---|---|---|---|
| pACYC/hdpA_gldA | 0.85 | 20.15 | 6.13 |
| Control group | 0 | 22.51 | 6.81 |

EXAMPLE 2

Manufacture of Microorganism having Ability to Produce 3-HP and Evaluation on Ability of Producing 3-HP in the Microorganism (1) Manufacture of an ET_BAB_Dc5 Vector In order to manufacture a microorganism capable of producing 3-hydroxypropionic acid (3-HP) from glycerol, an ET_BAB_Dc5 vector was manufactured.

Genes (i.e., dhaB1, dhaB2, and dhaB3 of SEQ ID NO: 5, 6, and 7, respectively) encoding GDH from genome DNA of *Ilyobacter polytropus* and genes (i.e., gdrA and gdrB of SEQ ID NO: 16 and 17, respectively) encoding GDR were used. The dhaB1, dhaB2, and dhaB3 genes used genome DNA of *I. polytropus* as a template, and dhaB123 was obtained as an amplification product by PCR amplification using a primer set of dhaB123_F (SEQ ID NO: 32) and dhaB123_R (SEQ ID NO: 33). The gdrA and gdrB genes used genomic DNA of *I. polytropus* as a template, and gdrAB was obtained as an amplification product by PCR amplification using a primer set of gdrAB_F (SEQ ID NO: 34) and gdrAB_R (SEQ ID NO: 35). The amplification products obtained therefrom were processed with restriction enzymes, i.e., BamHI and SacI, and then cloned in a pETDuet™-1 vector (Novagen).

Figure 3:
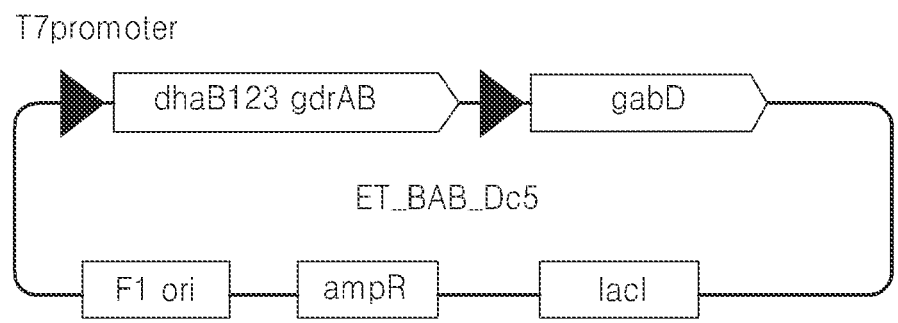
FIG. 3 is a cleavage map of a pETDuet/dhaB_gdrAB_gabD vector.
Figure 4:
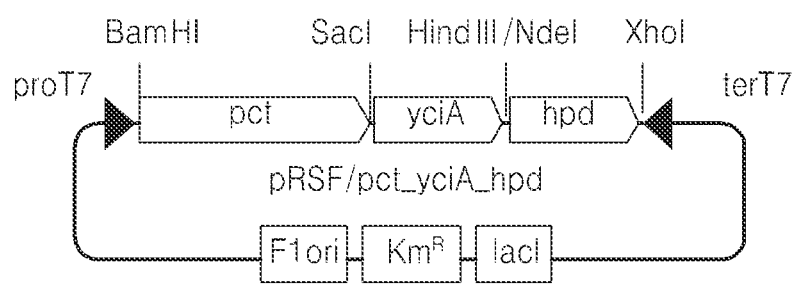
FIG. 4 is a cleavage map of a pRSF/pct_yciA_hpd vector.

In addition, genes (i.e., gabD of SEQ ID NO: 35) encoding SSADH from genomic DNA of *Cupriavidus necator* were obtained by PCR amplification using a primer set of gabD_F (SEQ ID NO: 37) and gabD_R (SEQ ID NO: 38). The amplification products obtained therefrom were processed with restriction enzymes, i.e., NdeI and KpnI, and then cloned in the vector above. As a result, a pETDuet-1/dhaB_gdrAB_gabD vector was obtained. FIG. 3 is a cleavage map of the pETDuet/dhaB_gdrAB_gabD vector.

(2) Evaluation on Ability to Produce 3-HP

The pETDuet/dhaB_gdrAB_gabD vector manufactured in step (1) of Example 2 was transformed into *E. coli* K(DE3) pACYC/hdpA_gldA strains capable of producing glycerol from glucose.

The strain was cultured using a 250 ml flask in a 50 ml medium (1.4 g/L of $MgSO_4$ $H_2O$, 17.4 g/L of $K_2HPO_4$, 3 g/L of $KH_2PO_4$, 4 g/L of $(NH_4)_2HPO_4$, 1.7 g/L of citric acid, 0.014 g/L of $ZnCl_2$, 0.041 g/L of $FeCl_2$ $H_2O$, 0.015 g/L of $MnCl_2$, 0.0015 g/L of $CuCl_2$, 0.003 g/L of $H_3BO_3$, 0.0025 g/L of $Na_2MoO_4$, 200 mg/L of nitriloacetic acid, 30 μg/L of sodium selenite, and 40 g/L of glycerol) at a temperature of 33° C. and at a rate of 250 rpm. In the beginning of the culture, the expression of 0.05 mM IPTG was induced when OD achieved 0.8 at a wavelength of 600 nm, and then 50 μM of Vitamin B12 was added thereto.

After culturing the culture medium for 24 hours, portions of the culture medium were harvested for measuring OD and pH, thereby identifying production of 3-HP by using HPLC (Waters). Once every 24 hours, the pH of the culture medium was corrected to pH 7.0 by using 4N NaOH. In HPLC analysis, an Aminex HPX-87H (300 mm×7.8 mm) column was used, and 0.5 mM of an aqueous solution of sulfuric acid containing 9% acetonitrile was used in a mobile phase. Here, HPLC had a flow rate of 0.4 ml/min and a temperature of 35° C. in the column. A detector device used a dual mode of RI and UV/VIS (210 nm). Glycerol was detected in 17.5 minutes out of 35 minutes in total.

Table 5 below shows produced amounts of 3-HP according to consumed amounts of glucose of *E. coli*. The recombinant strain consumed 22.84 g/L of glucose in 24 hours while it produced 0.51 g/L of 3-HP.

TABLE 5

| | Produced amounts of 3-HP (g/L) | Produced amounts of glycerol (g/L) | Consumed amounts of glucose (g/L) | OD |
|---|---|---|---|---|
| pACYC/hdpA_gldA + pETDuet/ dhaB_gdrAB_gabD4 | 0.51 | 0 | 22.84 | 5.32 |
| Control group | 0 | 0 | 23.03 | 7.02 |

EXAMPLE 3

Evaluation on Manufacture of Microorganisms Introduced with CoA Transferase, 3-HP CoA Dehydratase, and Acyl-CoA Thioester Hydrolase, and on Ability of the Microorganisms to Produce Acrylic Acid (1) Manufacture of a Vector for Introduction Genes (i.e., pct of SEQ ID NO: 23) encoding CoA transferase derived from *Megasphaera elsdenii* ATCC17753 used genome DNA of *Megasphaera elsdenii* ATCC17753 as a template, and were obtained by PCR amplification using a primer set of pct_F (SEQ ID NO: 39) and pct_R (SEQ ID NO: 40). PCR was performed in 25 cycles, each of which consists of a temperature of 95° C. for 30 seconds, at a temperature of 50° C. for 30 seconds, and a temperature of 72° C. for 3 minutes. The amplification products obtained therefrom were processed with restriction enzymes, i.e., BamHI and SacI, followed by being cloned into a pRSF-Duet™-1 vector (Novagen).

In addition, genes (i.e., yciA of SEQ ID NO: 25) encoding acyl-CoA thioester hydrolase derived from *E. coli* (e.g., *E. coli* K strains) used genome DNA of the *E. coli* K strains as a template and were obtained by PCR amplification using a primer set of yciA_F (SEQ ID NO: 41) and yciA_R (SEQ ID NO: 42). PCR was performed in 28 cycles, each of which consists of a temperature of 95° C. for 30 seconds, at a temperature of 50° C. for 30 seconds, and a temperature of 72° C. for 30 minutes. The obtained PCR products were then processed with restriction enzymes such as SacI and HindIII, followed by being cloned into a vector. As a result, a pRSFDuet/pct_yciA vector was obtained.

Genes (i.e., hpd of SEQ ID NO: 27) encoding 3-hydroxypropionyl-CoA derived from *Chloroflexus aurantiacus* ATCC29365 were obtained by PCR amplification using a primer set of hpdF (SEQ ID NO: 43) and hdpR (SEQ ID NO: 44). PCR was performed in 28 cycles, each of which consists of a temperature of 95° C. for 30 seconds, at a temperature of 54° C. for 30 seconds, and a temperature of 72° C. for 6 minutes. The obtained PCR products were then processed with restriction enzymes such as NdeI and XhoI, followed by being cloned into a vector. As a result, a pRSFDuet/pct_yciA_hpd vector was obtained.

(2) Evaluation on Ability to Produce Acrylic Acid

The pACYC/pct_yciA_hpd vector manufactured in step (1) was transformed into *E. coli* K (DE3) (pETDuet_dhaB_gdrAB_gabD and pACYC_hdpA_gldA), which is a strain producing 3-HP.

The *E. coli* to which the vector was introduced was cultured in an M9 minimal medium (1.4 g/L of MgSO$_4$ H$_2$O, 17.4 g/L of K$_2$HPO$_4$, 3 g/L of KH$_2$PO$_4$, 4 g/L of (NH$_4$)$_2$HPO$_4$, 1.7 g/L of citric acid, 0.014 g/L of ZnCl$_2$, 0.041 g/L of FeCl$_2$ H$_2$O, 0.015 g/L of MnCl$_2$, 0.0015 g/L of CuCl$_2$, 0.003 g/L of H$_3$BO$_3$, 0.0025 g/L of Na$_2$MoO$_4$, 200 mg/L of nitriloacetic acid, 30 µg/L of sodium selenite, and 40 g/L of glycerol) at a temperature of 30° C. until OB$_{600}$ achieved 0.6. 0.02 mM of IPTG was added thereto, and the medium was cultured again at a temperature of 30° C. for 24 hours. Then, the concentration of glycerol produced in the culture medium was measured. The culturing may be performed by shaking the medium in a 250 mL flask, and then the concentration of acrylic acid was calculated using high performance liquid chromatography (HPLC).

After culturing the culture medium for 24 hours, portions of the culture medium were extracted for measuring optical density and pH, thereby identifying production of 3-HP by using HPLC (Waters). Once every 24 hours, the pH of the culture medium was corrected to pH 7.0 by using 4N NaOH. In HPLC analysis, an Aminex HPX-87H (300 mm×7.8 mm) column was used, and 0.5 mM of an aqueous solution of sulfuric acid containing 9% acetonitrile was used in a mobile phase. Here, HPLC had a flow rate of 0.4 ml/min and a temperature of 35° C. in the column. A detector device used a dual mode of RI and UV/VIS (210 nm). Glycerol was detected in 18.2 minutes out of 35 minutes in total.

Table 6 below shows produced amounts of acrylic acid according to consumed amounts of glucose of the *E. coli*. The recombinant strain consumed 21.84 g/L of glucose in 24 hours while it produced 0.31 g/L of acrylic acid.

TABLE 6

| | Produced amount of acrylic acid (g/L) | Produced amount of 3-HP (g/L) | Produced amount of glycerol (g/L) | Consumed amount of glucose (g/L) | OD |
|---|---|---|---|---|---|
| pACYC/hdpA_gldA + pETDuet/ dhaB_gdrAB_gabD + pRSF/pct_yciA_hdp | 0.31 | 0 | 0 | 21.84 | 5.21 |
| Control group | 0 | 0 | 0 | 23.03 | 6.02 |

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising,"

"having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A recombinant microorganism comprising:
a polynucleotide encoding a haloacid dehydrogenase (HAD) superfamily dihydroxyacetone phosphate phosphatase (DHAPP), that catalyzes the conversion of dihydroxyacetone phosphate (DHAP) into dihydroxyacetone (DHA) and is from *Corynebacterium* genus and having phosphatase activity P-type ATPase; and
a polynucleotide encoding glycerol dehydrogenase (GLDH) categorized as EC 1.1.1.6 that catalyzes the conversion of DHA into glycerol,
a polynucleotide encoding glycerol dehydratase (GDH) categorized as EC 4.2.1.30 that catalyzes the conversion of glycerol into 3-hydroxypropionaldehyde (3-HPA); and
a polynucleotide encoding an aldehyde dehydrogenase (ALD) that catalyzes the conversion of 3-HPA into 3-hydroxypropionic acid (3-HP), wherein the ALD is a succinate semialdehyde dehydrogenase (SSADH) categorized as EC 1.2.1.24 or EC 1.2.1.16,
wherein at least one of the polynucleotides encoding the DHAPP, GLDH, GDH, or ALD are introduced via genetic manipulation, and
wherein the recombinant microorganism is a recombinant *Escherichia* microorganism.

2. The recombinant microorganism of claim 1, wherein the DHAPP comprises the amino acid sequence of SEQ ID NO: 1 and the GLDH comprises the amino acid sequence of SEQ ID NO: 3.

3. The recombinant microorganism of claim 1, wherein the polynucleotide encoding the DHAPP comprises the nucleotide sequence of SEQ ID NO: 2 and the polynucleotide encoding the GLDH comprises the nucleotide sequence of SEQ ID NO: 4.

4. The recombinant microorganism of claim 1, wherein the recombinant microorganism produces glycerol.

5. The recombinant microorganism of claim 1, wherein the recombinant microorganism produces 3-HP.

6. The recombinant microorganism of claim 1, wherein the GDH comprises the amino acid sequence of SEQ ID NO: 45, 46, or 47 and the SSADH comprises the amino acid sequence of SEQ ID NO: 8, 9, 10, or 48.

7. The recombinant microorganism of claim 1, wherein the polynucleotide encoding the GDH comprises the nucleotide sequence of SEQ ID NO: 5, 6, or 7 and the polynucleotide encoding the SSADH comprises the nucleotide sequence of SEQ ID NO: 11, 12, 13, or 36.

8. The recombinant microorganism of claim 1, further comprising a polynucleotide encoding glycerol dehydratase reactivase (GDR).

9. The recombinant microorganism of claim 8, wherein the GDR is gdrA from *Klebsiella pneumonia* or gdrB from *Ilyobacter polytropus*.

10. The recombinant microorganism of claim 8, wherein the GDR comprises the amino acid sequence of SEQ ID NO: 14, 15, 18, or 19.

11. The recombinant microorganism of claim 8, wherein the polynucleotide encoding the GDR comprises the nucleotide sequence of SEQ ID NO: 16, 17, 20, or 21.

12. The recombinant microorganism of claim 1, further comprising:
an enzyme that converts 3-HP into 3-HP-CoA; and
an enzyme that converts 3-HP-CoA into acryloyl-CoA.

13. The recombinant microorganism of claim 12, wherein the enzyme that converts 3-HP into 3-HP-CoA is a polypeptide having CoA transferase activity, a polypeptide belonging to EC 3.1.2.—that has 3-hydroxypropionly-CoA hydrolase activity, or a polypeptide belonging to EC 3.1.2.4 that has 3-hydroxyisobutyryl-CoA hydrolase activity, and
wherein the enzyme that converts 3-HP-CoA into acryloyl-CoA or acrylate is a polypeptide belonging to EC 4.2.1. that has 3-hydroxypropionyl-CoA dehydratase activity.

14. The recombinant microorganism of claim 1, wherein the DHAPP comprises an amino acid sequence having at least 70% sequence identity to SEQ ID NO: 1 and the GLDH comprises an amino acid sequence having at least 70% sequence identity to SEQ ID NO: 3.

15. The recombinant microorganism of claim 1, wherein the GDH comprises an amino acid sequence having at least 70% sequence identity to SEQ ID NO: 45, 46, or 47 and the SSADH comprises an amino acid sequence having at least 70% sequence identity to SEQ ID NO: 8, 9, 10, or 48.

16. A method of producing glycerol, the method comprising:
culturing the recombinant microorganism of claim 1 in a cell culture medium, whereby the microorganism produces glycerol; and
recovering glycerol from the culture.

17. The method of claim 16, wherein the culturing is performed under a microaerobic condition.

18. A method of making a microorganism that produces glycerol, the method comprising introducing into a microorganism that does not produce glycerol:
a polynucleotide encoding a haloacid dehydrogenase (HAD) superfamily dihydroxyacetone phosphate phosphatase (DHAPP) that catalyzes the conversion of dihydroxyacetone phosphate (DHAP) into dihydroxyacetone (DHA) and is from *Corynebacterium* genus and having phosphatase activity of P-type ATPase; and
a polynucleotide encoding glycerol dehydrogenase (GLDH) categorized as EC 1.1.1.6 that catalyzes the conversion of DHA into glycerol;
a polynucleotide encoding glycerol dehydratase (GDH) categorized as EC 4.2.1.30 that catalyzes the conversion of glycerol into 3-hydroxypropionaldehyde (3-HPA); and
a polynucleotide encoding an aldehyde dehydrogenase (ALD) that catalyzes the conversion of 3-HPA into 3-hydroxypropionic acid (3-HP), wherein the ALD is a succinate semialdehyde dehydrogenase (SSADH) categorized as EC 1.2.1.24 or EC 1.2.1.16,
thereby providing a microorganism that produces glycerol,
wherein the microorganism belongs to the genus *Escherichia*.

* * * * *